(12) United States Patent
Ariaans et al.

(10) Patent No.: US 12,180,552 B2
(45) Date of Patent: Dec. 31, 2024

(54) SITE-SPECIFIC CONJUGATION OF LINKER DRUGS TO ANTIBODIES AND RESULTING ADCS

(71) Applicant: Byondis B.V., Nijmegen (NL)

(72) Inventors: Gerardus Joseph Andreas Ariaans, Nijmegen (NL); Rudy Gerardus Elisabeth Coumans, Nijmegen (NL)

(73) Assignee: Byondis B.V., Nijmegen (NL)

( * ) Notice: Subject to any disclaimer, the term of this patent is extended or adjusted under 35 U.S.C. 154(b) by 728 days.

(21) Appl. No.: 17/409,462

(22) Filed: Aug. 23, 2021

(65) Prior Publication Data

US 2021/0388115 A1 Dec. 16, 2021

Related U.S. Application Data

(60) Division of application No. 16/457,244, filed on Jun. 28, 2019, now Pat. No. 11,104,968, which is a continuation of application No. 15/312,436, filed as application No. PCT/EP2015/061456 on May 22, 2015, now Pat. No. 10,407,743.

(30) Foreign Application Priority Data

May 22, 2014 (EP) .................................... 14169493

(51) Int. Cl.
| | | |
|---|---|---|
| *A61K 47/68* | (2017.01) | |
| *A61K 9/19* | (2006.01) | |
| *A61K 31/475* | (2006.01) | |
| *C07K 16/30* | (2006.01) | |
| *C07K 16/40* | (2006.01) | |

(52) U.S. Cl.
CPC .......... *A61K 47/6889* (2017.08); *A61K 9/19* (2013.01); *A61K 31/475* (2013.01); *A61K 47/6803* (2017.08); *A61K 47/68031* (2023.08); *A61K 47/6849* (2017.08); *A61K 47/6851* (2017.08); *A61K 47/6869* (2017.08); *C07K 16/30* (2013.01); *C07K 16/40* (2013.01); *C12Y 304/17021* (2013.01); *C07K 2317/51* (2013.01); *C07K 2317/515* (2013.01); *C07K 2317/55* (2013.01); *C07K 2317/56* (2013.01); *C07K 2317/77* (2013.01)

(58) Field of Classification Search
CPC .... A61K 9/19; A61K 31/475; A61K 47/6803; A61K 47/6849; A61K 47/6851; A61K 47/6869; A61K 47/6889; C07K 16/30; C07K 16/40; C07K 2317/51; C07K 2317/515; C07K 2317/55; C07K 2317/56; C07K 2317/77; C12Y 304/17021

See application file for complete search history.

(56) References Cited

U.S. PATENT DOCUMENTS

| | | | |
|---|---|---|---|
| 8,680,293 | B2 | 3/2014 | Beusker et al. |
| 8,889,868 | B2 | 11/2014 | Beusker et al. |
| 9,421,278 | B2 | 8/2016 | Dokter et al. |
| 9,427,480 | B2 | 8/2016 | Santin et al. |
| 11,008,400 | B2 * | 5/2021 | Van der Lee ...... A61K 47/6851 |
| 11,584,801 | B2 * | 2/2023 | Van der Lee ...... A61K 47/6851 |
| 2004/0120958 | A1 | 6/2004 | Bander et al. |
| 2006/0088522 | A1 | 4/2006 | Boghaert |
| 2008/0050310 | A1 * | 2/2008 | Ebens, Jr. ........ A61K 39/39558 424/1.49 |
| 2013/0224227 | A1 | 8/2013 | Beusker et al. |
| 2015/0216844 | A1 | 8/2015 | Beusker et al. |
| 2016/0052880 | A1 | 2/2016 | Beusker et al. |
| 2016/0324979 | A1 | 11/2016 | De Roo et al. |
| 2017/0007717 | A1 | 1/2017 | Santin et al. |
| 2017/0014525 | A1 | 1/2017 | Dokter et al. |

FOREIGN PATENT DOCUMENTS

| | | | |
|---|---|---|---|
| WO | WO 98/03873 A1 | 1/1998 | |
| WO | WO 02/098897 A2 | 12/2002 | |
| WO | WO 2005/084390 A2 | 9/2005 | |
| WO | WO 2006/031653 A2 | 3/2006 | |
| WO | WO-2006034488 A2 * | 3/2006 | ........... A61K 39/395 |
| WO | WO 2007/002222 A2 | 1/2007 | |
| WO | WO 2007/038658 A2 | 4/2007 | |
| WO | WO 2007/106744 A2 | 9/2007 | |
| WO | WO 2011/069019 A2 | 6/2011 | |
| WO | WO-2011133039 A2 * | 10/2011 | ........... A61K 31/437 |
| WO | WO 2013/093809 A1 | 6/2013 | |
| WO | WO 2015/185142 A1 | 12/2015 | |

(Continued)

OTHER PUBLICATIONS

Behrens, C.R. and Liu, B., "Methods for site-specific drug conjugation to antibodies," *mAbs* 6(1):46-53, Landes Bioscience, United States (Jan.-Feb. 2014).

Center for Biological Sequence Analysis (CBS), "SignalP 4.1 Server," cbs.dtu.dk, accessed at http://www.cbs.dtu.dk/services/SignalP/, accessed on Mar. 20, 2017, 2 pages.

Doronina, S.O., et al., "Enhanced Activity of Monomethylauristatin F through Monoclonal Antibody Delivery: Effects of Linker Technology on Efficacy and Toxicity," *Bioconjugate Chem.* 17(1):114-124, American Chemical Society, United States (2006).

(Continued)

*Primary Examiner* — Nelson B Moseley, II
*Assistant Examiner* — Alyssa Rae Stonebraker
(74) *Attorney, Agent, or Firm* — Buscher Patent PLLC

(57) ABSTRACT

The present invention relates to antibody-drug conjugates (ADCs) wherein a linker drug is site-specifically conjugated to an antibody through an engineered cysteine, and their use as a medicament, notably for the treatment of human solid tumours and haematological malignancies, in particular breast cancer, gastric cancer, colorectal cancer, urothelial cancer, ovarian cancer, uterine cancer, lung cancer, mesothelioma, liver cancer, pancreatic cancer, prostate cancer, and leukaemia.

19 Claims, 7 Drawing Sheets

Specification includes a Sequence Listing.

(56) References Cited

FOREIGN PATENT DOCUMENTS

WO    WO 2016/046173 A1    3/2016

OTHER PUBLICATIONS

Edelman, G.M., et al., "The covalent structure of an entire γG immunoglobulin molecule," *Proc. Natl. Acad. Sci. USA* 63(1):78-85, National Academy of Sciences, United States (1969).

Fan, X., et al., "A single proteolytic cleavage within the lower hinge of trastuzumab reduces immune effector function and in vivo efficacy," *Breast Cancer Res.* 14(4):R116, BioMed Central Ltd., England, 13 pages (2012).

Junutula, J.R., et al., "Site-specific conjugation of a cytotoxic drug to an antibody improves the therapeutic index," *Nature Biotechnology* 26(8):925-932, Nature Publishing Group, England (2008).

Kabat, E.A., et al., in *Sequences of Proteins of Immunological Interest*, 5$^{th}$ Edition, Public Health Service, National Institutes of Health, Bethesda, MD, NIH publication No. 91-3242, pp. 662, 680, 689 (1991).

Krieger, E., et al., "Improving physical realism, stereochemistry, and side-chain accuracy in homology modeling: four approaches that performed well in CASP8," *Proteins* 77(Suppl 9):114-122, Wiley-Liss, United States (2009).

Kung Sutherland, M.S., et al., "SGN-CD33A: a novel CD33-targeting antibody-drug conjugate using a pyrrolobenzodiazepine dimer is active in models of drug-resistant AML," *Blood* 122(8):1455-1463, The American Society of Hematology, United States (2013).

Trott, 0. and Olson, A.J., "AutoDock Vina: improving the speed and accuracy of docking with a new scoring function, efficient optimization, and multithreading," *J. Comput. Chem.* 31(2):455-461, Wiley, United States (2010).

Yasara Biosciences, "About Yasara—Watching Nature@Work," yasara.org, accessed at http://yasara.org/index.html, accessed on Mar. 20, 2017, 3 pages.

Zeuthen, J., et al., "Characterization of a human ovarian teratocarcinoma-derived cell line," *Int. J. Cancer* 25(1):19-32, Wiley-Liss, United States (1980).

International Preliminary Report on Patentability and Written Opinion for International Application No. PCT/EP2015/061456, The International Bureau of WIPO, Geneva, Switzerland, issued on Nov. 22, 2016, 8 pages.

International Search Report for International Application No. PCT/EP2015/061456, European Patent Office, Rijswijk, Netherlands, mailed on Jul. 3, 2015, 5 pages.

Brezski, R.J., et al., "Tumor-associated and microbial proteases compromise host IgG effector functions by a single cleavage proximal to the hinge," *Proc. Natl. Acad. Sci. USA* 106(42):17864-17869, National Academy of Sciences, United States (2009).

Wei Li et al., "Antibody Aggregation: Insights from Sequence and Structure," *Antibodies* 2016, 5, 19, pp. 1-23.

Robert P. Lyon et al., "Reducing hydrophobicity of homogeneous antibody-drug conjugates improves pharmacokinetics and therapeutic index," *Nature Biotechnology*, Brief Communication, published online Jun. 15, 2015, pp. 1-4.

Kamath and Iyer, "Preclinical Pharmacokinetic Considerations for the Development of Antibody Drug Conjugates," *Pharm Res* (2015) 32: 3470-3479.

Kamath and Iyer, "Challenges and advances in the assessment of the disposition of antibody-drug conjugates," *Biopharm. Drug Dispos.* 37: 66-77 (2016).

Lyon et al., "Reducing hydrophobicity of homogeneous antibody-drug conjugates improves pharmacokinetics and therapeutic index," Nature Biotechnology, vol. 33, No. 7, Jul. 2015.

\* cited by examiner

SITE-SPECIFIC CONJUGATION OF LINKER DRUGS TO ANTIBODIES AND RESULTING ADCS

CROSS REFERENCE TO RELATED APPLICATIONS

The present application is a divisional under 35 U.S.C. §§ 121 and 120 of application Ser. No. 16/457,244, filed Jun. 28, 2019, which is a continuation under 35 U.S.C. § 120 of U.S. application Ser. No. 15/312,436, filed Nov. 18, 2016, now U.S. Pat. No. 10,407,743, which is a U.S. national stage application under 35 U.S.C. § 371 of PCT International Application No. PCT/EP2015/061456 filed May 22, 2015, which claims the benefit of priority to European Application No. 14169493.5, filed on May 22, 2014; the disclosure of each prior U.S. application is incorporated by reference herein in its entirety.

REFERENCE TO SEQUENCE LISTING SUBMITTED VIA EFS-WEB

This application includes an electronically submitted sequence listing in .txt format. The .txt file contains a sequence listing entitled "P1664US03_PB-067_ST25.txt" created on Aug. 23, 2021 and is 28,672 bytes in size. The sequence listing contained in this .txt file is part of the specification and is hereby incorporated by reference herein in its entirety.

FIELD OF THE INVENTION

The present invention relates to antibody-drug conjugates (ADCs) wherein a linker drug is site-specifically conjugated to an antibody through an engineered cysteine, and their use in the treatment of human solid tumours and haematological malignancies, in particular breast cancer, gastric cancer, colorectal cancer, urothelial cancer, ovarian cancer, uterine cancer, lung cancer, mesothelioma, liver cancer, pancreatic cancer, prostate cancer, and leukaemia.

BACKGROUND OF THE PRESENT INVENTION

Antibody-drug conjugates (ADCs) are an emerging class of targeted therapeutics having an improved therapeutic index over traditional chemotherapy. Drugs and linkers have been the focus of ADC development, in addition to (monoclonal) antibody (mAb) and target selection. Recently, however, the importance of conjugate homogeneity was realized. The conventional methods for drug attachment to an antibody lead to a heterogeneous mixture, and some individual constituents of that mixture can have poor in vivo performance. Newer methods for site-specific drug attachment lead to more homogeneous conjugates and allow control of the site of drug attachment. These subtle improvements can have profound effects on in vivo efficacy and/or in vivo safety and thereby on the therapeutic index. Methods for site-specific drug conjugation to antibodies are comprehensively reviewed by C. R. Behrens and B. Liu in mAbs, Vol. 6, Issue 1, 2014, pages 1-8.

Conventional ADCs are typically produced by conjugating the linker drug to the antibody through the side chains of either surface-exposed lysines or free cysteines generated through reduction of interchain disulfide bonds. Because antibodies contain many lysine residues and cysteine disulfide bonds, conventional conjugation typically produces heterogeneous mixtures that present challenges with respect to analytical characterization and manufacturing. Furthermore, the individual constituents of these mixtures exhibit different physicochemical properties and pharmacology with respect to their pharmacokinetic, efficacy, and safety profiles, hindering a rational approach to optimizing this modality.

These two conventional techniques for chemical modification of antibodies were used to construct the two ADCs with current FDA marketing approvals. Brentuximab vedotin (Adcetris™, Seattle Genetics) consists of an anti-CD30 monoclonal antibody conjugated to the highly cytotoxic drug monomethyl auristatin E (MMAE) via modification of native cysteine side chain thiols. The manufacture involves partial reduction of the solvent-exposed interchain disulfides followed by modification of the resulting thiols with maleimide-containing linker drugs. For brentuximab vedotin, the thiols were modified with mc-vc-PAB-MMAE, which incorporates a cathepsin B protease cleavage site (vc, valine-citrulline) and a self-immolative linker (PAB, para-aminobenzyloxycarbonyl) between the maleimide group (mc, maleimidocaproyl) and the cytotoxic drug (MMAE). The cysteine attachment strategy results in maximally two drugs per reduced disulfide. Most human IgG molecules have four solvent-exposed disulfide bonds, and so a range of from zero to eight drugs per antibody is possible. The exact number of drugs per antibody is determined by the extent of disulfide reduction and the number of molar equivalents of linker drug used in the ensuing conjugation reaction. Full reduction of all four disulfide bonds gives a homogeneous construct with eight drugs per antibody, while a partial reduction typically results in a heterogeneous mixture with zero, two, four, six, or eight drugs per antibody. Brentuximab vedotin has an average of about 4 drugs per antibody.

The other ADC with current FDA approval is ado-trastuzumab emtansine (T-DM1, Kadcyla™, Roche/Genentech), which was constructed by coupling the anti-HER2 monoclonal antibody trastuzumab to the cytotoxic drug maytansine through modification of lysine side chain amines. This version of maytansine (DM1) was modified to include a thiol that could be attached to a maleimide linker. A bifunctional linker (SMCC, succinimidyl 4-(N-maleimidomethyl)cyclohexane-1-carboxylate) with a maleimide at one end and an N-hydroxysuccinimidyl (NHS) ester at the other end was reacted with lysine primary amine side chains to form a stable amide bond. The modified maytansine (DM1) was then attached to the antibody through conjugation to the maleimide end of the bifunctional linker. In contrast to the linker utilized in brentuximab vedotin, this linker has no (protease) cleavage site and thus requires lysosomal degradation of the antibody part of the ADC to liberate the active DM1-linker-lysine metabolite. The attachment method resulted in a heterogeneous mixture of conjugates with an average of 3.5 drugs per antibody. Compared with the cysteine method described above, this strategy gave a more heterogeneous mixture because 20 to 40 lysine residues were found to be modified, whereas only maximally 8 different cysteine residues are modified using the native cysteine modification method.

Recently, it was reported that the pharmacological profile of ADCs may be improved by applying site-specific conjugation technologies that make use of surface-exposed cysteine residues engineered into antibodies that are then conjugated to a linker drug, resulting in site-specifically conjugated ADCs with defined drug-to-antibody ratios (DARs). Relative to the heterogeneous mixtures created using conventional lysine and cysteine conjugation methodologies, site-specifically conjugated ADCs have generally demonstrated at least equivalent in vivo potency, improved PK, and an expanded therapeutic window.

The first site-specific conjugation approach was developed at Genentech by introducing a cysteine residue using site-directed mutagenesis at positions showing high thiol reactivity as elaborated in WO2006/034488. This common practice in protein modification was more complicated in an antibody because of the various native cysteine residues already present. Introducing the extra cysteine residue in an unsuitable position could result in improper formation of interchain disulfide bonds and therefore improper folding of the antibody. Engineered cysteine residues in suitable positions in the mutated antibody are often capped by other thiols, such as cysteine or glutathione, to form disulfides.

Drug attachment to the mutant residues was achieved by reducing both the native interchain and mutant disulfides, then re-oxidizing the native interchain cysteines using a mild oxidant such as $CuSO_4$ or dehydroascorbic acid, followed by standard conjugation of the liberated mutant cysteine with a linker drug. Under optimal conditions, two drugs per antibody will be attached (if one cysteine is engineered into the heavy chain or light chain of the mAb). The engineered cysteine method proved to be suitable for developing the site-specific ADC SGN-CD33A (Seattle Genetics), which recently entered a Phase I dose-escalation clinical study as a treatment for acute myeloid leukaemia (AML), as well as a Phase Ib clinical trial in combination with standard of care chemotherapy, including cytarabine and daunorubicin. This ADC comprises a cleavable dipeptide linker (i.e., valine-alanine) and a DNA-cross-linking, pyrrolobenzodiazepine (PBD) dimer as the drug linked to heavy chain position S239C in the Fc part of IgG1 mAb h2H12 (DAR 1.9; Sutherland et al. Blood 2013; 122(8):1455-1463).

Whereas in WO2006/034488 specifically surface accessible valine, alanine and serine residues not involved in antigen binding interactions and distant from the existing interchain disulfide bonds were substituted to obtain engineered cysteine residues with high thiol reactivity, WO2014/124316 from Novartis specifically focuses on the identification of surface accessible sites in the constant regions of the antibody heavy and light chains, at which sites substitution for a cysteine residue enables efficient conjugation of payloads and provides conjugates with high stability.

In addition to the engineered cysteine conjugation strategy, other methods for site-specific attachment of drugs have been developed. Pfizer demonstrated a new technique for conjugation using microbial transglutaminase to couple an amine-containing drug to an engineered glutamine on the antibody. Transglutaminase is an enzyme that catalyzes amide bond formation between the acyl group of a glutamine side chain and the primary amine of a lysine side chain.

In addition to enzymatic conjugation, orthogonal chemistry conjugation has also been used to site-specifically modify a wide variety of proteins using non-natural amino acids (notably technologies from Ambrx and Sutro Biopharma). In particular, p-acetylphenyl-alanine and p-azidomethyl-L-phenylalanine were chosen as the non-natural amino acids, because they, respectively, contain a ketone and an azide functional group that is not found in any of the 20 natural amino acid side chains. This allows for specific modification of the ketone cq. azide groups without interference from other amino acids. This method provided an additional route for constructing ADCs with a maximum of two drugs per antibody (per one such non-natural amino acid).

In all of the prior art methods disclosed thus far, the emphasis was put on site-specifically conjugating linker drugs at surface/solvent-exposed positions, at positions showing high thiol reactivity, and at positions in specifically the constant regions of monoclonal antibodies, with the aim of improving homogeneity and pharmacokinetic properties. Even though the above-described conventional lysine and cysteine conjugation methods have led to FDA-approved antibody-drug conjugates and they are being used for constructing most of a large number of ADCs currently in preclinical and clinical trials, there is still a need for new conjugation strategies with the aim to (further) improve the physicochemical, pharmacokinetic, pharmacological, and/or toxicological properties of ADCs to obtain ADCs having acceptable antigen binding properties, in vivo efficacy, therapeutic index, and/or stability.

BRIEF DESCRIPTION OF THE PRESENT INVENTION

The present invention relates to antibody-drug conjugates (ADCs) wherein a linker drug is site-specifically conjugated to an antibody through an engineered cysteine at one or more specific positions of said antibody, and their use in the treatment of human solid tumours and haematological malignancies, in particular breast cancer, gastric cancer, colorectal cancer, urothelial cancer, ovarian cancer, uterine cancer, lung cancer, mesothelioma, liver cancer, pancreatic cancer, prostate cancer, and leukaemia.

DETAILED DESCRIPTION OF THE PRESENT INVENTION

Figure 1A:
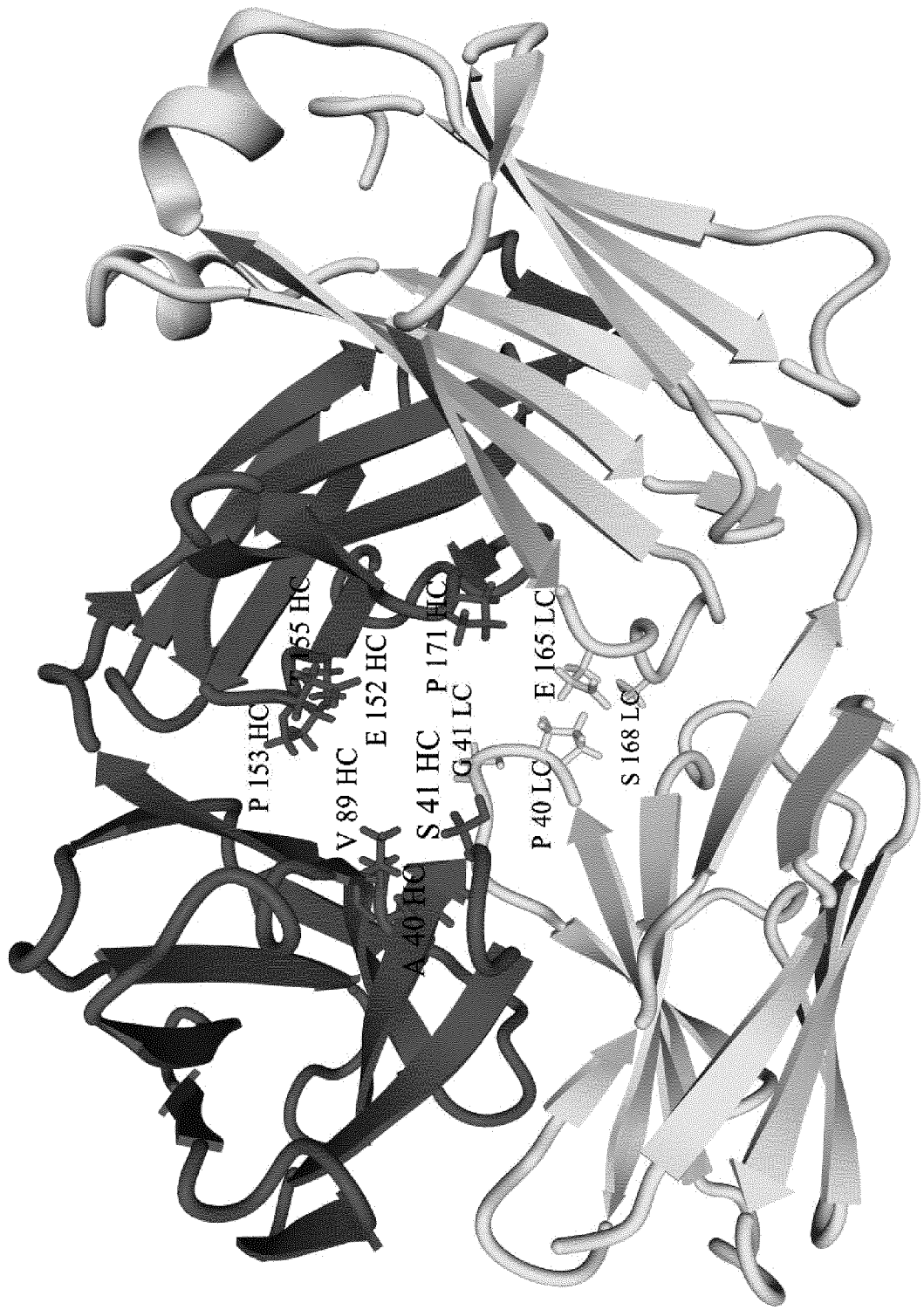
FIG. 1A. Identification of suitable linker drug conjugation positions in the Fab part of an antibody.

Antibody-drug conjugates (ADCs) are emerging as a new class of anticancer therapeutics that combine the efficacy of small-molecule therapeutics with the targeting ability of antibodies. By combining these two components into a single new molecular entity, highly cytotoxic small molecule drugs can be delivered to cancerous target tissues, thereby enhancing efficacy while reducing the potential systemic toxic side effects of the small molecule.

Antibodies have been conjugated to a variety of cytotoxic drugs, including small molecules that bind DNA (e.g. anthracyclines), alkylate or crosslink DNA (e.g. duocarmycins or pyrrolobenzodiazepine dimers, respectively), cause DNA strand breaks (e.g. calicheamicins) or disrupt microtubules (e.g. maytansinoids and auristatins).

The present invention relates to an antibody-drug conjugate (ADC) compound wherein a linker drug is site-specifically conjugated to an antibody through an engineered cysteine at one or more positions of said antibody selected from heavy chain 40, 41, 89 (Kabat numbering), 152, 153, 155, 171, 247, 297, 339, 375 and 376 (Eu numbering), and light chain 40, 41 (Kabat numbering), 165 and 168 (Eu numbering).

In one embodiment, the present invention relates to an antibody-drug conjugate (ADC) compound wherein a linker drug is site-specifically conjugated to an antibody through an engineered cysteine at one or more positions of said antibody selected from heavy chain 40, 41, 89, 152, 153, 155, 171, 247, 297, 339 and 375, and light chain 40, 41, and 165.

In a particularly preferred embodiment, the present invention relates to an antibody-drug conjugate compound wherein a linker drug is site-specifically conjugated to an antibody through an engineered cysteine at one or more positions of said antibody selected from heavy chain 40, 41 and 89 (according to Kabat numbering) and light chain 40 and 41 (according to Kabat numbering).

As the focus in earlier work on site-specific ADCs was on finding conjugation positions that show good reactivity with the linker drug, and at the same time have a low risk of forming disulfide bonds between antibodies (leading to aggregation) or disturbing the antibody structure (so-called disulfide bridge shuffling), the effects on hydrophobicity of the conjugates in relation to the conjugation site have not been evaluated. In addition, the focus has primarily been on finding suitable sites in the constant regions of the antibody, as modification of the variable regions of an antibody is generally thought to be associated with a high risk of partial or complete loss of antigen binding.

The current inventors, however, have focused on influencing the hydrophobicity characteristics of site-specific ADCs.

An in silico method, employing the YASARA software package (yasara.org, see: Krieger et al. Proteins 2009; 77 Suppl 9: 114-122), was used to identify sites of strong interaction of the linker drug with the antibody. Suitable locations show a minimal increase in the hydrophobic surface. In the vicinity of the thus-identified interaction sites suitable residues (i.e., with sufficient accessibility) to convert to cysteines were identified. In this approach no limitation was made to the constant regions of the antibody, also the variable region amino acids were considered if not in the vicinity of antigen binding sites. Locations in the variable domain of the Fab part turned out to be preferable.

Docking of linker drugs into the Fab and Fc models of various antibodies was simulated with the commonly used VINA algorithm (Trott O and Olson AJ. J. Comput. Chem. 2010; 31: 455-461) as implemented in YASARA. The antibody Fab and Fc models used were obtained from X-ray structures or by homology modeling using YASARA.

Figure 1B:
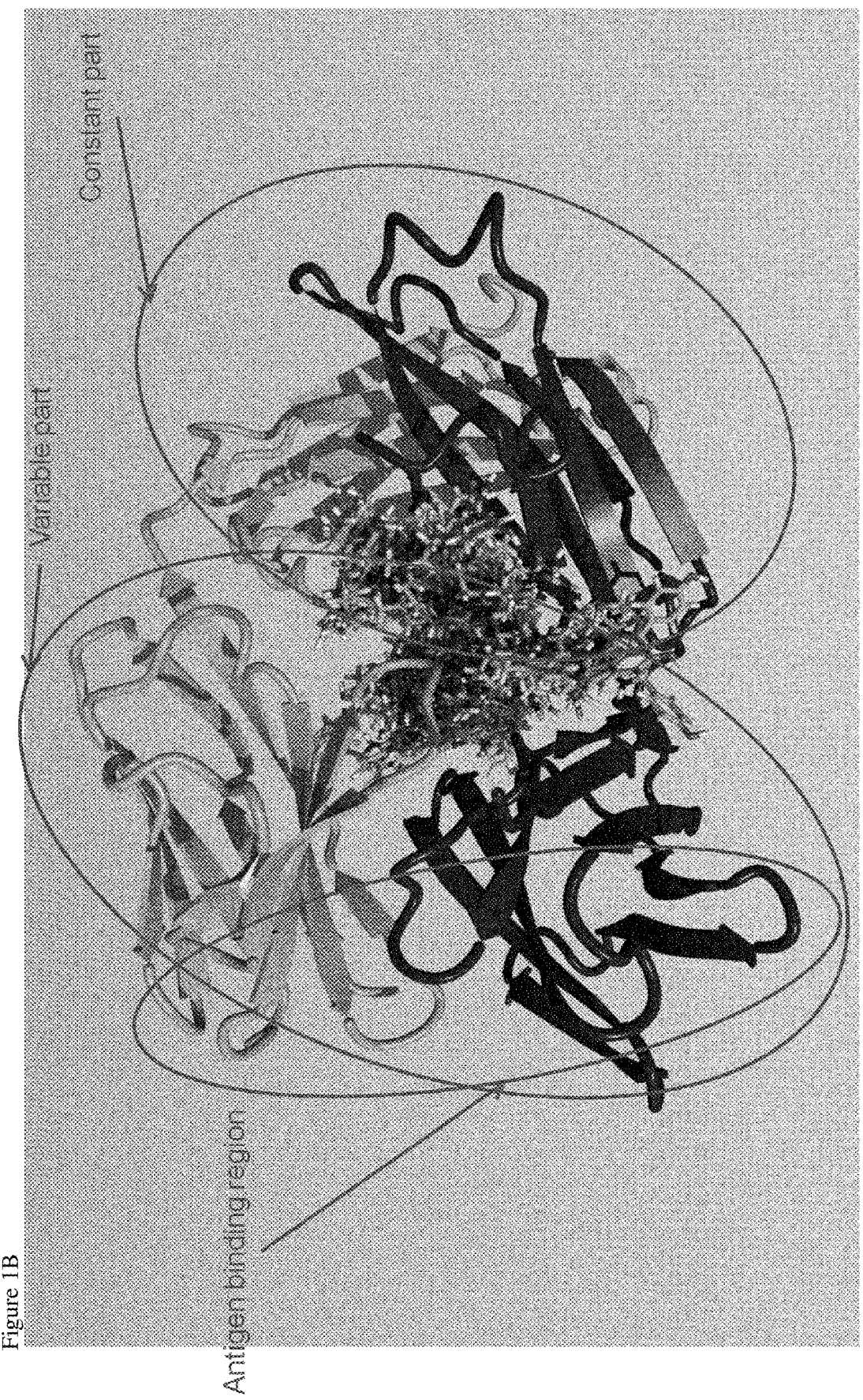
FIG. 1B. Docking of duocarmycin linker drug vc-seco-DUBA in the Fab cavity of an antibody (overlay of multiple vc-seco-DUBA dockings)
Figure 1C:
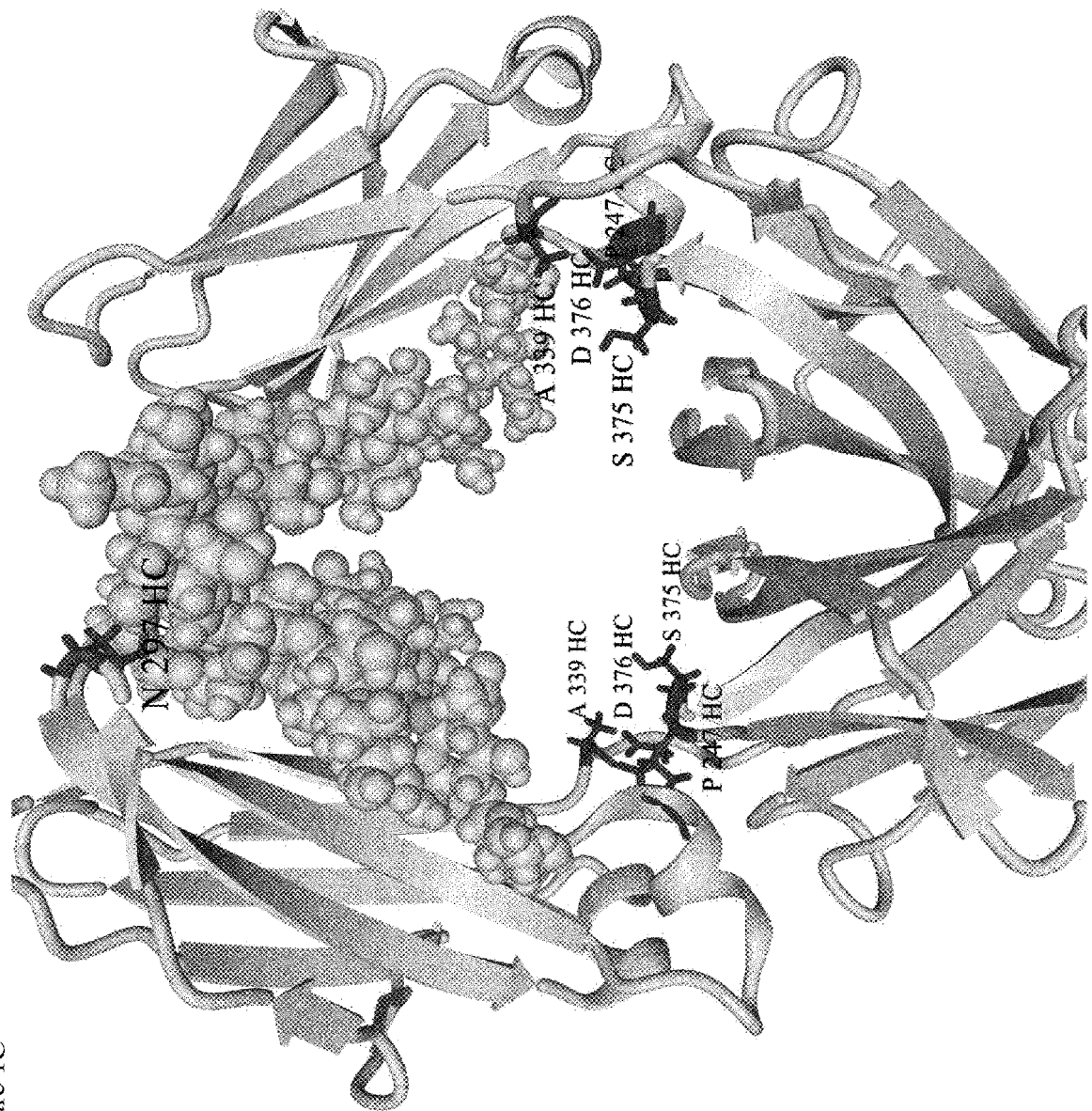
FIG. 1C. Identification of suitable linker drug conjugation positions in the Fc part of an antibody.
Figure 1D:
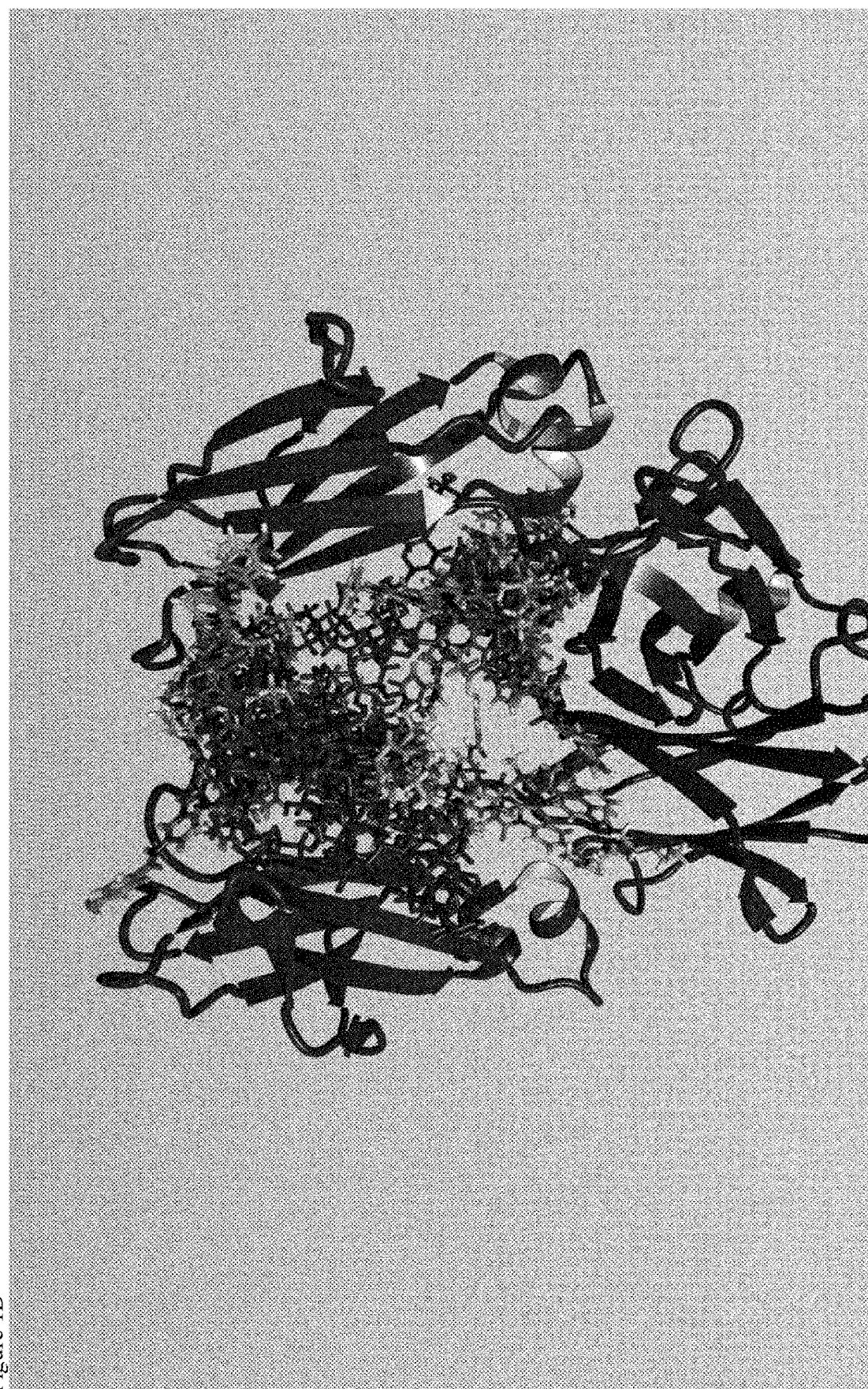
FIG. 1D. Docking of duocarmycin linker drug vc-seco-DUBA in the Fc cavity of an antibody (overlay of multiple vc-seco-DUBA dockings) FIG. 2A. In vivo efficacy of engineered cysteine anti-PSMA (VH S41C) ADC (SYD1091) versus vehicle control, comparator engineered cysteine anti-PSMA (CH T120C) ADC (SYD1035), and non-engineered anti-PSMA (wild-type) wt ADC (SYD998) at 2 mg/kg each.

The duocarmycin type linker drugs, e.g. vc-seco-DUBA (i.e., SYD980; an ADC compound thereof is depicted in formula II), were shown to have a strong preference for binding in cavities which are present in all antibody structures (see FIGS. 1B and 1D for the Fab and the Fc part of an antibody, respectively). Multiple suitable conjugation positions for linker drug attachment were identified in and in close proximity to these cavities, i.e., with good accessibility of engineered cysteines at these locations (see FIGS. 1A and 1C for the Fab and the Fc part of an antibody, respectively).

In the context of the present invention, Kabat numbering is used for indicating the amino acid positions of engineered cysteines in the heavy chain (HC) and light chain (LC) variable regions and Eu numbering is used for indicating the positions in the heavy chain and light chain constant regions of the antibody. In view of the sequence variability in the variable regions of antibodies, the exact amino acid to be substituted by cysteine can be different for different antibodies. For most antibodies, in particular IgG antibodies, in the heavy chain of the variable region (VH), there usually is an A or S at position 40, a P at position 41 and a V at position 89 and in the light chain of the variable region (VL), there usually is a P at position 40 and a G at position 41. In the heavy chain of the constant regions (CH1, CH2 and CH3), there is normally an E at position 152, a P at position 153, a T at position 155, a P at position 171, a P at position 247, an N at position 297, an A at position 339, an S at position 375 and a D at position 376, and in the light chain of the κ constant region (CL), there is normally an E at position 165 and an S at position 168. In the five λ light chain isotype constant regions (CL), there is normally an S at position 165 and an S at position 168.

The expression "Kabat numbering" refers to the numbering system used for heavy chain variable domains or light chain variable domains of the compilation of antibodies in Kabat, E. A. et al., Sequences of Proteins of Immunological Interest, 5th Ed. Public Health Service, National Institutes of Health, Bethesda, MD (1991). Using this numbering system, the actual linear amino acid sequence may contain fewer or additional amino acids corresponding to a shortening of, or insertion into, a framework region (FR) or complementary determining region (CDR) of the variable domain. The Kabat numbering of residues may be determined for a given antibody by alignment at regions of homology of the sequence of the antibody with a "standard" Kabat numbered sequence.

The expression "Eu numbering" refers to the Eu index as in Kabat, E. A. et al., Sequences of Proteins of Immunological Interest, 5th Ed. Public Health Service, National Institutes of Health, Bethesda, MD, NIH publication no. 91-3242, pp. 662, 680, 689 (1991). The "Eu index as in Kabat" refers to the residue numbering of the human IgG1 Eu antibody (Edelman, G. M. et al., Proc. Natl. Acad. Sci. USA, 63, 78-85 (1969)).

Heavy chain positions 40, 41 and 89 are located in the variable region and positions 152, 153, 155, 171, 247, 297, 339, 375 and 376 are located in the constant region of the antibody. Light chain positions 40 and 41 are located in the variable region and positions 165 and 168 are located in the constant region of the antibody.

Heavy chain positions 40, 41, 89, 152, 153, 155 and 171 and light chain positions 40, 41, 165 and 168 are located in the Fab part and heavy chain positions 247, 297, 339, 375 and 376 are located in the Fc part of the antibody.

In accordance with the present invention, the term "engineered cysteine" means replacing a non-cysteine amino acid in the heavy chain or light chain of an antibody by a cysteine. As is known by the person skilled in the art, this can be done either at the amino acid level or at the DNA level, e.g. by using site-directed mutagenesis.

The present inventors surprisingly have found that the site-specifically conjugated ADC compounds of the present invention show improved physicochemical, pharmacological and/or pharmacokinetic properties, as compared to ADCs wherein the linker drug is conjugated through native interchain disulfide bonds of the antibody and, moreover, as compared to engineered cysteine ADCs wherein the linker drug is conjugated at positions disclosed in the prior art from the ones specifically claimed in this patent application. The ADC compounds in accordance with the present invention have binding properties similar to the naked antibodies, good in vivo efficacy, an increased therapeutic index and/or improved stability. Notably, it was found that the ADC compounds are generally less hydrophobic and less susceptible to cathepsin B cleavage and therefore likely also to other intra- or extracellular enzymes/proteases in the tumour mass (tumour microenvironment) than ADCs that are site-specifically conjugated at different positions, but still show similar in vitro cytotoxicity. Unexpectedly, ADCs in accordance with the present invention show improved in vivo efficacy in a tumour xenograft animal model as compared to ADCs that are site-specifically conjugated at other positions.

Without wishing to be bound by any theory, the present inventors have found that when linker drugs are conjugated at the specific positions of the antibody as claimed herein, said linker drug fits into either the Fab cavity that is formed by the CH1, VH, VL and CL domains of the antibody or the Fc cavity that is formed by the two CH2 and two CH3 domains of the antibody. In an IgG1 antibody the top of the Fc cavity is formed by the glycoside/carbohydrate that is attached to the heavy chain position N297. As a result, the linker drug (which typically is more hydrophobic than the antibody) is shielded from the hydrophilic aqueous environment surrounding the antibody and the ADC as such is less hydrophobic as compared to ADCs wherein the linker drug is conjugated through native disulfide bonds of the antibody and is much less hydrophobic as compared to ADCs wherein the linker drug is site-specifically conjugated at different positions that are not presently claimed and where the linker drug is forced to the outside of the antibody, i.e., is pointed in a direction away from the antibody.

In one particular embodiment, the present invention relates to an antibody-drug conjugate (ADC) compound wherein a linker drug is site-specifically conjugated to an antibody through an engineered cysteine at one or more positions of said antibody selected from heavy chain 40, 41, 152, 153, 247, 339 and 375, and light chain 40, 41, and 165.

In another embodiment, the present invention relates to an antibody-drug conjugate (ADC) compound wherein a linker drug is site-specifically conjugated to an antibody through an engineered cysteine at one or more positions of said antibody selected from heavy chain 40, 41, 89, 247, 297 and 376, and light chain 40 and 41.

In one embodiment, the present invention relates to an antibody-drug conjugate (ADC) compound wherein a linker drug is site-specifically conjugated to an antibody through an engineered cysteine at one or more positions of said antibody selected from heavy chain 40, 41, 89, 152, 153, 155 and 171, and light chain 40, 41, 165 and 168 in the Fab part of said antibody.

In another embodiment, the present invention relates to an antibody-drug conjugate (ADC) compound wherein a linker drug is site-specifically conjugated to an antibody through an engineered cysteine at one or more positions of said antibody selected from heavy chain 40, 41, 152 and 153, and light chain 40, 41 and 165 in the Fab part of said antibody.

Modification of the variable part of an antibody is generally avoided as it can lead to partial or complete loss of antigen binding properties. However, contrary to the general expectations, it was found that specific residues in the framework regions of the heavy and light chains of the antibody are both suitable for conjugation and do not lead to (significant) reduction of antigen binding after conjugation of the linker drug. Therefore, in a particularly preferred embodiment, the present invention relates to an antibody-drug conjugate (ADC) compound wherein said engineered cysteine is at one or more positions of said antibody selected from heavy chain 40, 41 and 89 and light chain 40 and 41 in the Fab part of said antibody. Preferably, said engineered cysteine is at heavy chain position 40 or 41 and/or light chain position 40 or 41, more preferably at heavy chain position 41 and/or light chain position 40 or 41, most preferably at heavy chain position 41. As it is known from the literature that tumour-associated proteases in the tumour microenvironment can partially cleave the Fc constant domains, under the hinge region, conjugation in the Fab part is preferred over conjugation in the Fc part. Cleavage of the Fc constant domains would result in loss of Fc-conjugated linker drugs, which in turn could lead to a decreased activity of the ADC in vivo. (Fan et al. Breast Cancer Res. 2012; 14: R116 and Brersky et al. PNAS 2009; 106: 17864-17869). Moreover, conjugation to these positions in the Fab part also enables the use of antigen binding fragments.

In a specific embodiment, the antibody-drug conjugate (ADC) compound of the above preferred embodiment may further comprise an additional engineered cysteine at one or more positions of the antibody selected from heavy chain 152, 153, 155, 171, 339 and 375, and light chain 165 and 168. Preferably said further engineered cysteine is at heavy chain position 375 in the Fc part of said antibody.

In accordance with the present invention, the one or more cysteine residues can be engineered into the antibody by using conventional molecular cloning techniques or the heavy chain or light chain domain(s) of the antibody carrying the cysteine mutation(s) can be synthesized as such using known (peptide or DNA) synthesis equipment and procedures.

In accordance with the present invention, any linker drug known in the art of ADCs can be used for site-specific conjugation to an antibody, provided it has a chemical group which can react with the thiol group of an engineered cysteine, typically a maleimide or haloacetyl group. Suitable linker drugs may comprise a duocarmycin, calicheamicin, pyrrolobenzodiazepine (PBD) dimer, maytansinoid or auristatin derivative as a cytotoxic drug. Either a cleavable or a non-cleavable linker may be used in accordance with the present invention. Suitable examples of maytansinoid drugs include DM1 and DM4. Suitable examples of auristatin drugs include MMAE and MMAF.

These abbreviations are well-known to the skilled artisan. Examples of suitable linker drugs known to the person skilled in the art include mc-vc-PAB-MMAE (also abbreviated as mc-vc-MMAE and vc-MMAE), mc-MMAF, and mc-vc-MMAF. Preferably, the linker used is a cleavable linker, such as valine-citrulline (vc) or valine-alanine (va).

The generic molecular structures of a vc-MMAE ADC and mc-MMAF ADC are depicted below.

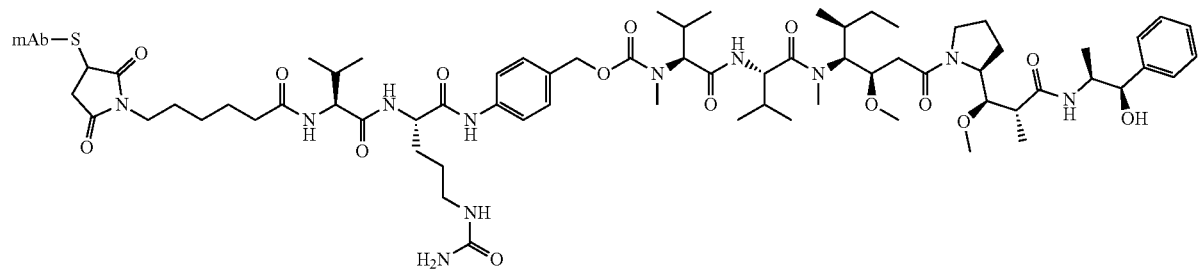

Molecular Structure of Vc-MMAE Linked to a mAb

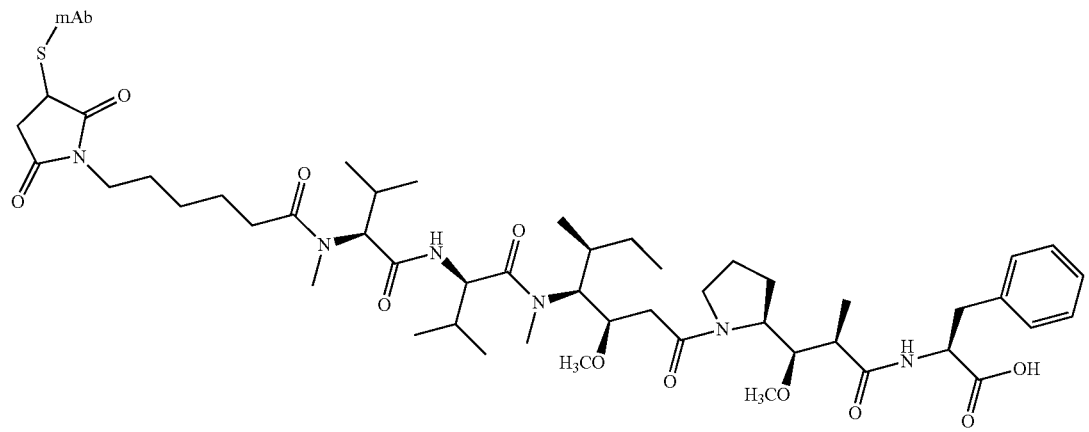

Molecular Structure of Mc-MMAF Linked to a mAb

In one embodiment, the present invention relates to an ADC compound wherein said linker drug comprises a duocarmycin derivative.

Duocarmycins, first isolated from a culture broth of *Streptomyces* species, are members of a family of antitumour antibiotics that include duocarmycin A, duocarmycin SA, and CC-1065. These extremely potent agents allegedly derive their biological activity from an ability to sequence-selectively alkylate DNA at the N3 position of adenine in the minor groove, which initiates a cascade of events that terminates in an apoptotic cell death mechanism.

WO2011/133039 discloses a series of linker drugs comprising a duocarmycin derivative of CC-1065. Suitable linker-duocarmycin derivatives to be used in accordance with the present invention are disclosed on pages 182-197. The chemical synthesis of a number of these linker drugs is described in Examples 1-12 of WO2011/133039.

In one embodiment, the present invention relates to a compound of formula (I)

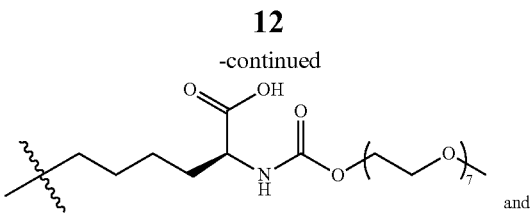
and

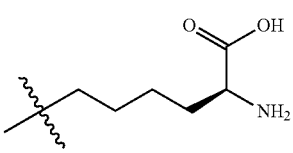

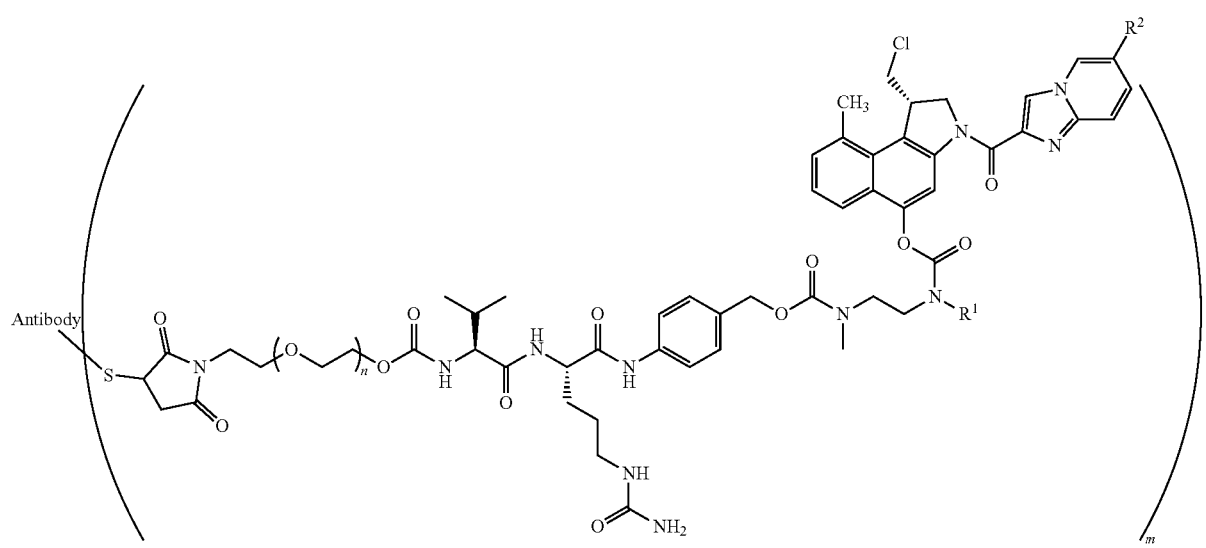

(I)

wherein n is 0-3, preferably 0-1, m represents an average DAR of from 1 to 6, preferably of from 1 to 4, $R^1$ is selected from y is 1-16, and $R^2$ is selected from

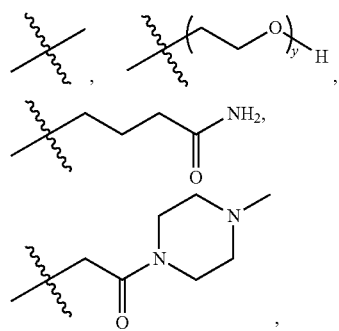

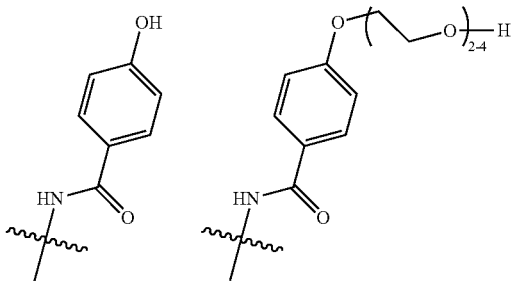

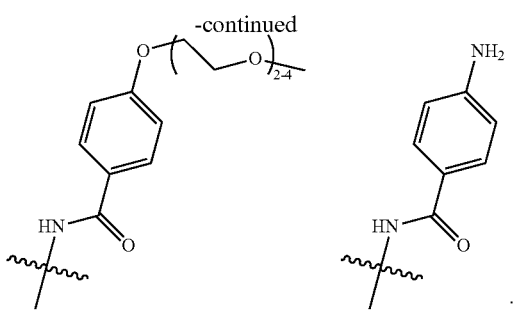

In the structural formulae shown in the present specification, n represents an integer from 0 to 3, while m represents an average drug-to-antibody ratio (DAR) of from 1 to 6. As is well-known in the art, the DAR and drug load distribution can be determined, for example, by using hydrophobic interaction chromatography (HIC) or reversed phase high-performance liquid chromatography (RP-HPLC). HIC is particularly suitable for determining the average DAR.

Compounds of the formula (I) in accordance with the present invention can be obtained according to methods and procedures that are well known to a person skilled in the art. Suitable methods for site-specifically conjugating linker drugs can for example be found in Examples 7 and 8 of WO2005/084390, which describe complete reduction strategies for (partial) loading of antibodies with the linker drug vc-MMAE, in Examples 11 and 12 of WO2006/034488, which describe site-specific conjugation of a maytansine (DM1)-comprising linker drug, and in Doronina et al. Bioconjugate Chem. 17 (2006): 114-124, which describes the conjugation with mc-MMAF.

Conjugation to two or more of the engineered cysteine sites of the present invention allows for the preparation of ADCs comprising hydrophobic drug classes with a higher DAR, notably DAR 4, without getting too much aggregate.

In accordance with a particular embodiment of the present invention, one or two engineered cysteines can be incorporated into the heavy chain and/or light chain of the antibody, under optimal reaction conditions resulting in an ADC compound having a DAR of 2 or 4, respectively. When one engineered cysteine is introduced, it can be located either in the Fab or in the Fc part of the antibody. It is preferred to introduce said cysteine in the Fab part of the antibody at position HC 40, 41, 89, 152 or 153 or LC 40, 41 or 165, preferably HC 40, 41 or 89 or LC 40, 41 or 165, more preferably HC 40 or 41 or LC 40 or 41, even more preferably HC 41 or LC 40 or 41, most preferably HC 41. When two engineered cysteines are introduced, these two cysteines can both be located in the Fab or in the Fc part of the antibody or, preferably, one can be in the Fab part, preferably HC 40, 41, 152 or 153 or LC 40, 41 or 165, more preferably HC 40 or 41 or LC 40 or 41, even more preferably HC 41 or LC 40 or 41, most preferably HC 41, and the other can be in the Fc part of the antibody, preferably HC 247, 297, 339 or 375, more preferably HC 339 or 375, most preferably HC 375. When two engineered cysteines are introduced in the Fab part of the antibody, one cysteine residue may be introduced in the heavy chain and the other cysteine is introduced in the light chain of the antibody, e.g. HC 40 or 41 and LC 40 or 41. In addition, when two engineered cysteines are introduced in the Fab part of the antibody, one cysteine residue may be introduced at one of the specific positions as identified in the present invention, e.g. HC 40 or 41 or LC 40 or 41, and the other may be located at a surface-exposed (i.e., not herein claimed) engineered cysteine position leading to a higher DAR and still acceptable hydrophobicity.

In a particular embodiment, the present invention relates to a compound of the formula (I) as disclosed hereinabove, wherein n is 0-1, m represents an average DAR of from 1 to 6, preferably of from 1 to 4, more preferably of from 1 to 2, most preferably of from 1.5 to 2, $R^1$ is selected from

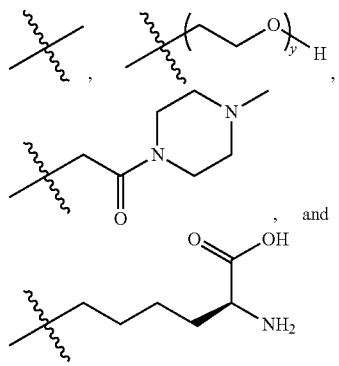

y is 1-16, preferably 1-4, and
$R^2$ is selected from

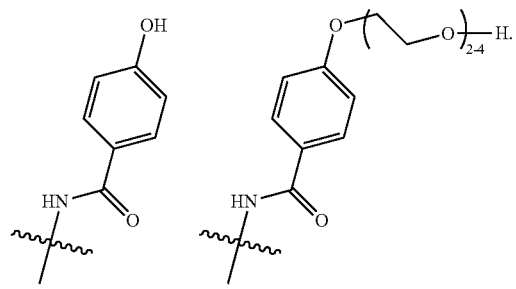

In a specific embodiment, the present invention relates to a compound of the structural formula (I) as disclosed hereinabove, wherein n is 0-1, m represents an average DAR of from 1.5 to 2, $R^1$ is

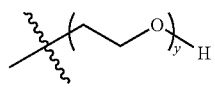

y is 1-4, and $R^2$ is selected from

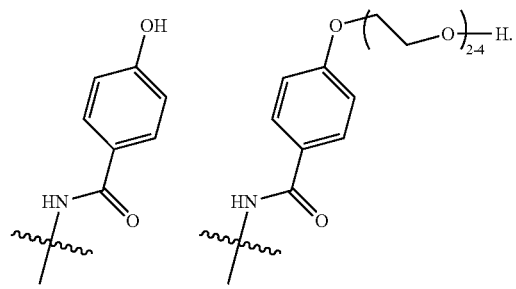

In a particularly preferred embodiment, the present invention relates to a compound of formula (II)

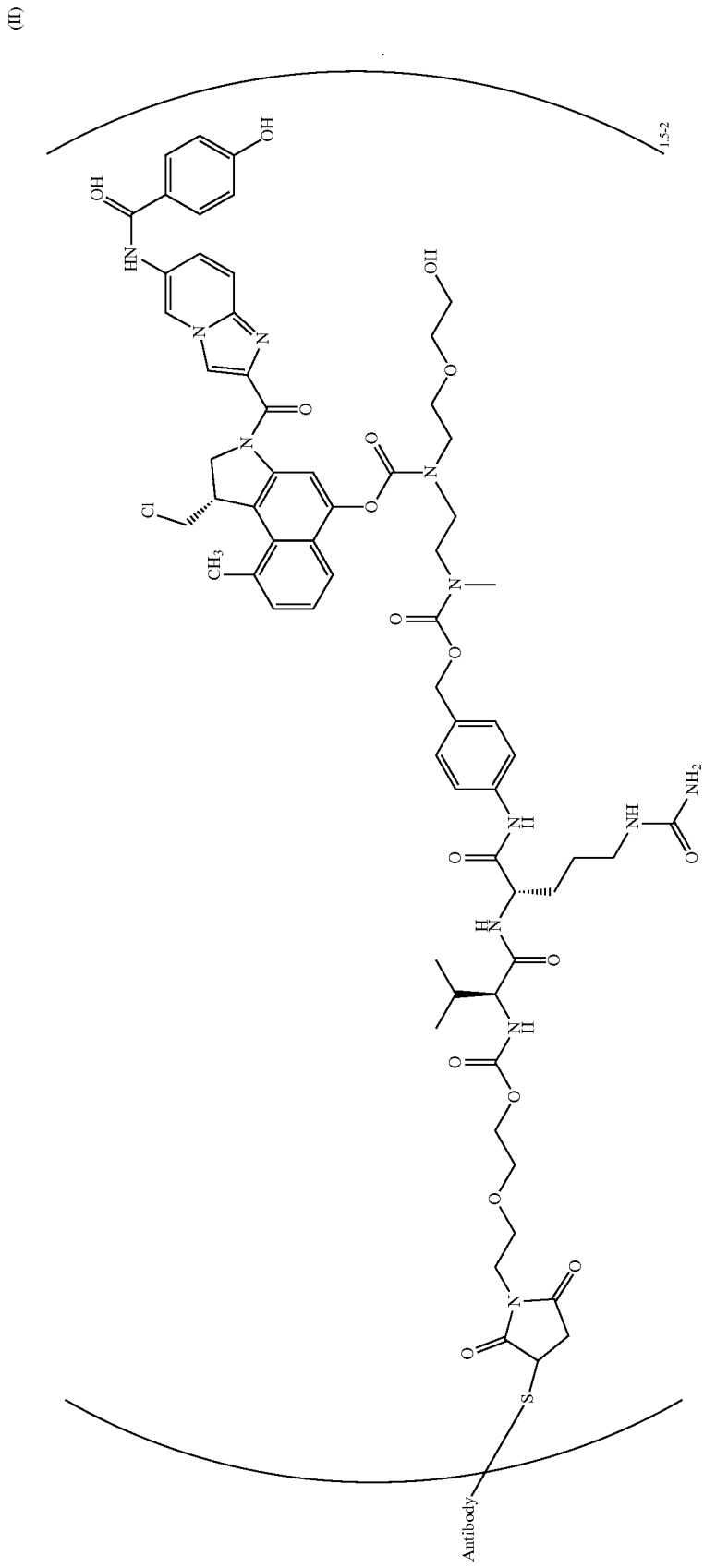

In accordance with the present invention, any antibody—particularly any antibody known to have therapeutic activity or any antibody known in the art of ADCs—or any antigen binding fragment thereof can be used for site-specific conjugation of a linker drug at the specific antibody positions claimed herein. Said antibody can be an IgA, IgD, IgE, IgG or IgM antibody. Said antibody can have κ (kappa) light chains or λ (lambda) light chains. Said IgG antibody can be an IgG1, IgG2, IgG3 or IgG4 antibody. Preferably, the antibody binds to a(n) antigen target that is expressed in or on the cell membrane (e.g., on the cell surface) of a tumour cell, more preferably, the antibody is internalised by the cell after binding to the (antigen) target, after which the toxin is released intracellularly. Preferably, the antibody is an IgG antibody, more preferably an IgG1 antibody, most preferably an IgG1 antibody having κ light chains. Preferably, the IgG antibody carries a native glycoside/carbohydrate moiety attached at N297 of the heavy chain of the antibody.

Suitable antibodies include an anti-annexin A1 antibody, an anti-CD19 antibody, an anti-CD22 antibody, an anti-CD30 antibody, an anti-CD33 antibody, an anti-CD37 antibody, an anti-CD38 antibody, an anti-CD44 antibody, an anti-CD47 antibody, an anti-CD56 antibody, an anti-CD70 antibody, an anti-CD74 antibody, an anti-CD79 antibody, an anti-CD115 antibody, an anti-CD123 antibody, an anti-CD138 antibody, an anti-CD203c antibody, an anti-CD303 antibody, an anti-CEACAM antibody, an anti-CLL-1 antibody, an anti-c-MET (or anti-HGFR) antibody, an anti-Cripto antibody, an anti-DLL3 antibody, an anti-EGFR antibody, an anti-EPCAM antibody, an anti-EphA2 antibody, an anti-EphB3 antibody, an anti-ETBR antibody, an anti-FcRL5 antibody, an anti-FOLR1 antibody, an anti-GCC antibody, an anti-GPNMB antibody, an anti-Her2 antibody, an anti-HMW-MAA antibody, an anti-integrin antibody, an anti-Lewis A like carbohydrate antibody, an anti-Lewis Y antibody, an anti-LIV1 antibody, an anti-mesothelin antibody, an anti-MN antibody, an anti-MUC1 antibody, an anti-MUC16 antibody, an anti-NaPi2b antibody, an anti-Nectin-4 antibody, an anti-PSMA antibody, an anti-SIRPα antibody, an anti-SLC44A4 antibody, an anti-STEAP-1 antibody, an anti-5T4 (or anti-TPBG, trophoblast glycoprotein) antibody, an anti-Tag72 antibody, an anti-TF (or anti-tissue factor) antibody, an anti-TROP2 antibody and an anti-VLA antibody.

Preferably, the antibody is an anti-annexin A1 antibody, an anti-CD115 antibody, an anti-CD123 antibody, an anti-CLL-1 antibody, an anti-c-MET antibody, an anti-MUC1 antibody, an anti-PSMA antibody, an anti-5T4 antibody or an anti-TF antibody. More preferably, the antibody is an anti-PSMA antibody or an anti-5T4 antibody.

The antibody to be used in accordance with the present invention preferably is a monoclonal antibody (mAb) and can be a chimeric, humanized or human mAb. More preferably, in accordance with the present invention a humanized or human mAb is used, even more preferably a humanized or human IgG antibody, most preferably a humanized or human IgG1 mAb. Preferably, said antibody has κ (kappa) light chains, i.e., a humanized or human IgG1-κ antibody.

In humanized antibodies, the antigen-binding CDRs in the variable regions are derived from antibodies from a non-human species, commonly mouse, rat or rabbit. These non-human CDRs are placed within a human framework (FR1, FR2, FR3 and FR4) of the variable region, and are combined with human constant regions. Like human antibodies, these humanized antibodies can be numbered according to the Kabat numbering system. The present invention particularly relates to an ADC compound wherein said engineered cysteine is at a position selected from VH 40, VH 41, VH 89, VL 40 or VL 41 in the human framework (i.e., VH 40, VH 41, VL 40 and VL 41 are in the middle of FR2, VH 89 is in FR3) of a humanized antibody, more particularly at VH 40, VH 41, VL 40 or VL 41, even more particularly at VH 41, VL 40 or VL 41, especially at VH 41.

In accordance with the present invention, these specific residues in the framework regions are both suitable for conjugation of a linker drug and do not lead to significant reduction of antigen binding properties of the antibody after conjugation of the linker drug. Furthermore, these sites are not only suitable in antibodies, but also in any antigen binding fragments thereof.

In one particular embodiment, the present invention relates to an ADC compound as described hereinabove wherein said antibody is an anti-annexin A1 antibody, an anti-CD115 antibody, an anti-CD123 antibody, an anti-CLL-1 antibody, an anti-c-MET antibody, an anti-MUC1 antibody, an anti-PSMA antibody, an anti-5T4 antibody or an anti-TF antibody and said linker drug comprises a duocarmycin derivative, preferably an ADC compound in accordance with formula (I) or (II).

In a further particular embodiment, the present invention relates to an ADC compound as described hereinabove wherein said antibody is an anti-PSMA (monoclonal) antibody or an anti-5T4 (monoclonal) antibody and said linker drug comprises a duocarmycin derivative, preferably an ADC compound in accordance with formula (I) or (II).

In a preferred embodiment, the present invention relates to an ADC compound as described hereinabove, wherein said linker drug comprises a duocarmycin derivative and is conjugated at position 41 of the heavy chain variable region of an anti-PSMA (monoclonal) antibody or an anti-5T4 (monoclonal) antibody, most preferably an ADC compound according to formula (II). Suitable anti-PSMA antibodies are described in WO98/03873 (e.g., Example 12), WO02/098897 (e.g., FIGS. 1-2), WO2007/002222 (e.g., Table 1) and WO2011/069019 (e.g., FIG. 2). Suitable anti-5T4 antibodies include H8, which is described in WO2006/031653, and the A1 and A3 antibodies which are described in WO2007/106744, as well as any antibodies binding to the same epitope as these known antibodies.

In a more preferred embodiment, the heavy chain of the anti-PSMA antibody comprises the amino acid sequence of SEQ ID NO:2 and the light chain of the anti-PSMA antibody comprises the amino acid sequence of SEQ ID NO:5. More preferably, the heavy chain of the anti-PSMA antibody comprises the amino acid sequences of SEQ ID NO:2 and SEQ ID NO:3, and the light chain of the anti-PSMA antibody comprises the amino acid sequences of SEQ ID NO:5 and SEQ ID NO:6.

In a particularly preferred embodiment, the present invention relates to an ADC compound of formula (II), wherein the antibody is an anti-PSMA antibody, the heavy chain of said anti-PSMA antibody comprising the amino acid sequence of SEQ ID NO:2 and the light chain of said anti-PSMA antibody comprising the amino acid sequence of SEQ ID NO:5. More preferably, the heavy chain of said anti-PSMA antibody comprises the amino acid sequences of SEQ ID NO:2 and SEQ ID NO:3, and the light chain of said anti-PSMA antibody comprises the amino acid sequences of SEQ ID NO:5 and SEQ ID NO:6.

In another more preferred embodiment, the heavy chain of the anti-5T4 antibody comprises the amino acid sequence of SEQ ID NO:8 and the light chain of the anti-5T4 antibody comprises the amino acid sequence of SEQ ID NO:11. More preferably, the heavy chain of the anti-5T4 antibody comprises the amino acid sequences of SEQ ID NO:8 and SEQ ID NO:9, and the light chain of the anti-5T4 antibody comprises the amino acid sequences of SEQ ID NO:11 and SEQ ID NO:6.

In a particularly preferred embodiment, the present invention relates to an ADC compound of formula (II), wherein the antibody is an anti-5T4 antibody, the heavy chain of said anti-5T4 antibody comprising the amino acid sequence of SEQ ID NO:8 and the light chain of said anti-5T4 antibody comprising the amino acid sequence of SEQ ID NO:11. More preferably, the heavy chain of said anti-5T4 antibody comprises the amino acid sequences of SEQ ID NO:8 and SEQ ID NO:9, and the light chain of said anti-5T4 antibody comprises the amino acid sequences of SEQ ID NO:11 and SEQ ID NO:6.

The present invention further relates to an ADC compound as described hereinabove for use as a medicament.

In one embodiment, the present invention relates to an ADC compound as described hereinabove for use in the treatment of human solid tumours and haematological malignancies.

In a further embodiment, the present invention relates to an ADC compound as described hereinabove for use in the treatment of human solid tumours selected from the group consisting of breast cancer, gastric cancer, colorectal cancer, urothelial cancer (e.g. bladder cancer), ovarian cancer, uterine cancer, lung cancer (especially non-small cell lung cancer and small-cell lung cancer), mesothelioma (especially malignant pleural mesothelioma), liver cancer, pancreatic cancer, and prostate cancer.

In a preferred embodiment, the present invention relates to an ADC compound as described hereinabove, particularly a compound comprising an anti-PSMA (monoclonal) antibody and a duocarmycin derivative linker drug, for use in the treatment of prostate cancer.

In another preferred embodiment the present invention relates to an ADC compound as described hereinabove, particularly a compound comprising an anti-5T4 (monoclonal) antibody and a duocarmycin derivative linker drug, for use in the treatment of human solid tumours selected from the group consisting of breast cancer, gastric cancer, colorectal cancer, ovarian cancer, lung cancer (especially non-small cell lung cancer (NSCLC) and small-cell lung cancer (SCLC)), and malignant pleural mesothelioma.

In yet a further embodiment, the present invention relates to an ADC compound as described hereinabove for use in the treatment of human haematological malignancies, particularly leukaemia, selected from the group consisting of acute lymphoblastic and myeloid leukaemia (ALL and AML, respectively).

The present invention further relates to a pharmaceutical composition comprising an ADC compound as described hereinabove and one or more pharmaceutically acceptable excipients. Typical pharmaceutical formulations of therapeutic proteins such as monoclonal antibodies and (monoclonal) antibody-drug conjugates take the form of lyophilized cakes (lyophilized powders), which require (aqueous) dissolution (i.e., reconstitution) before intravenous infusion, or frozen (aqueous) solutions, which require thawing before use.

Typically, the pharmaceutical composition is provided in the form of a lyophilized cake. Suitable pharmaceutically acceptable excipients for inclusion into the pharmaceutical composition (before freeze-drying) in accordance with the present invention include buffer solutions (e.g. citrate, histidine or succinate containing salts in water), lyoprotectants (e.g. sucrose, trehalose), tonicity modifiers (e.g. sodium chloride), surfactants (e.g. polysorbate), and bulking agents (e.g. mannitol, glycine). Excipients used for freeze-dried protein formulations are selected for their ability to prevent protein denaturation during the freeze-drying process as well as during storage. As an example, the sterile, lyophilized powder single-use formulation of Kadcyla™ (Roche) contains—upon reconstitution with Bacteriostatic or Sterile Water for Injection (BWFI or SWFI)—20 mg/mL ado-trastuzumab emtansine, 0.02% w/v polysorbate 20, 10 mM sodium succinate, and 6% w/v sucrose with a pH of 5.0.

The present invention also relates to the use of a compound or a pharmaceutical composition as described hereinabove for the treatment of human solid tumours and haematological malignancies as described hereinabove.

The present invention further relates to the use of a sequentially or simultaneously administered combination of a compound or a pharmaceutical composition as described hereinabove with a therapeutic antibody and/or a chemotherapeutic agent, for the treatment of human solid tumours and haematological malignancies as described hereinabove.

In one embodiment of the present invention, the therapeutic antibody is adecatumumab, alemtuzumab, amatuximab, bevacizumab, cetuximab, denosumab, etaracizumab, farletuzumab, gemtuzumab, labetuzumab, mapatumumab, minretumomab, nimotuzumab, nivolumab, oregovomab, panitumumab, pemtumomab, pertuzumab, ramucirumab, sibrotuzumab, trastuzumab or volociximab and the chemotherapeutic agent is i) an alkylating agent, particularly nitrogen mustards, such as mechlorethamine, chlorambucil, cyclophosphamide, ifosfamide and melphalan, nitrosoureas, such as streptozocin, carmustine and lomustine, alkyl sulfonates, such as busulfan, triazines, such as dacarbazine and temozolomide, ethylenimines, such as thiotepa and altretamine, or platinum drugs, such as cisplatin, carboplatin and oxaliplatin, ii) an anti-metabolite, particularly 5-fluorouracil, 6-mercaptopurine, capecitabine, cytarabine, floxuridine, fludarabine, gemcitabine, hydroxyurea, methotrexate or pemetrexed, iii) an anti-tumour antibiotic, particularly daunorubicin, doxorubicin, epirubicin, idarubicin, actinomycin D, bleomycin, mitomycin-C or mitoxantrone, iv) a topoisomerase inhibitor, particularly topoisomerase I inhibitors, such as topotecan and irinotecan, or topoisomerase II inhibitors, such as etoposide, teniposide and mitoxantrone, v) a mitotic inhibitor, particularly taxanes, such as paclitaxel, cabazitaxel and docetaxel, epothilones, such as ixabepilone, vinca alkaloids, such as vinblastine, vincristine and vinorelbine, or estramustine, vi) a signalling cascade inhibitor, particularly mTOR (mammalian target of rapamycin) inhibitors, such as temsirolimus and everolimus, or tyrosine kinase inhibitors, such as gefitinib, erlotinib, imatinib, pazopanib, ceritinib, crizotinib, lapatinib and afatinib, vii) a corticosteroid, particularly prednisone, methylprednisolone or dexamethasone, viii) a hormonal therapeutic agent, particularly androgen receptor modulating agents, such as bicalutamide, enzalutamide and abiraterone acetate, anti-oestrogens, such as tamoxifen, or aromatase inhibiting or steroid modifying agents, such as anastrozole, letrozole, fulvestrant and exemestane, ix) a PARP inhibitor, particularly olaparib, or x) another chemotherapy drug, particularly L-asparaginase or bortezomib. The person skilled in the art will have no difficulty in selecting suitable combination therapies for use in the treatment of human solid tumours and haematological malignancies as described hereinabove.

In another embodiment of the present invention, particularly in case of an anti-PSMA ADC compound comprising a duocarmycin derivative linker drug, the therapeutic antibody is bevacizumab, denosumab, pertuzumab or trastuzumab and the chemotherapeutic agent is a topoisomerase II inhibitor, particularly mitoxantrone, a mitotic inhibitor, particularly a taxane, more particularly cabazitaxel or docetaxel, a corticosteroid, particularly prednisone, or a hormonal therapeutic agent, particularly an androgen receptor modulating agent, more particularly enzalutamide or abiraterone acetate.

In yet another embodiment of the present invention, particularly in case of an anti-5T4 ADC compound comprising a duocarmycin derivative linker drug, the therapeutic antibody is bevacizumab, cetuximab, nivolumab, or ramucirumab and the chemotherapeutic agent is an alkylating agent, particularly a platinum drug, more particularly cisplatin or carboplatin, an anti-metabolite, particularly gemcitabine or pemetrexed, a topoisomerease II inhibitor, particularly etoposide, a mitotic inhibitor, particularly a taxane or a vinca alkaloid, more particularly paclitaxel or docetaxel, or vinblastine or vinorelbine, or a signalling cascade inhibitor, particularly a tyrosine kinase inhibitor, more particularly erlotinib, ceritinib, crizotinib or afatinib.

In a further embodiment of the present invention, particularly in case of an anti-5T4 ADC compound comprising a duocarmycin derivative linker drug, the therapeutic antibody is bevacizumab and the chemotherapeutic agent is an alkylating agent, particularly a nitrogen mustard, a platinum drug or a triazine, more particularly cyclophosphamide, ifosfamide, cisplatin, or temozolomide, an anti-tumour antibiotic, particularly doxorubicin, an anti-metabolite, particularly gemcitabine, a topoisomerease I or II inhibitor, particularly topotecan, irinotecan or etoposide, or a mitotic inhibitor, particularly a taxane or a vinca alkaloid, more particularly paclitaxel or docetaxel, or vincristine or vinorelbine.

In yet a further embodiment of the present invention, particularly in case of an anti-5T4 ADC compound comprising a duocarmycin derivative linker drug, the therapeutic antibody is amatuximab and the chemotherapeutic agent is an alkylating agent, particularly a platinum drug, more particularly cisplatin or carboplatin, an anti-metabolite, particularly gemcitabine or pemetrexed, or a mitotic inhibitor, particularly a vinca alkaloid, more particularly vinorelbine.

A therapeutically effective amount of the compounds in accordance with the present invention lies in the range of about 0.01 to about 15 mg/kg body weight, particularly in the range of about 0.1 to about 10 mg/kg body weight, more particularly in the range of about 0.3 to about 10 mg/kg body weight. This latter range corresponds roughly to a flat dose in the range of 20 to 800 mg of the ADC compound. The compound of the present invention may be administered weekly, bi-weekly, three-weekly or monthly, for example weekly for the first 12 weeks and then every three weeks until disease progression. Alternative treatment regimens may be used depending upon the severity of the disease, the age of the patient, the compound being administered, and such other factors as would be considered by the treating physician.

EXAMPLES

Transient Expression of Engineered Cysteine (Mutant) Antibodies
1a) Preparation of cDNAs
The cDNA sequence for the heavy chain was obtained from the amino acid sequences of a leader sequence (SEQ ID NO:1), the heavy chain variable region of an anti-PSMA antibody (SEQ ID NO:2, Kabat numbering, having a cysteine residue at position 41) and the human IgG1 heavy chain constant region (SEQ ID NO:3, sequential numbering, Eu numbering starting at alanine 118) by back-translating the combined amino acid sequences into a cDNA sequence optimized for expression in human cells (*Homo sapiens*) (SEQ ID NO:4).

Similarly, the cDNA sequence for the light chain was obtained from the amino acid sequences of a secretion signal (SEQ ID NO:1), the light chain variable region of an anti-PSMA antibody (SEQ ID NO:5, Kabat numbering), and the human κ Ig light chain constant region (SEQ ID NO:6, sequential numbering) by back-translating the combined amino acid sequences into a cDNA sequence optimized for expression in human cells (*Homo sapiens*) (SEQ ID NO:7).

Similarly, the cDNA sequence for the heavy chain of the anti-5T4 antibody H8-HC41 (SEQ ID NO:10) was obtained from the amino acid sequences of a leader sequence (SEQ ID NO:1), the heavy chain variable region of the H8 antibody (SEQ ID NO:8, sequential numbering, having a cysteine residue at position 41) and the human IgG1 heavy chain constant region (SEQ ID NO:9, sequential numbering, Eu numbering starting at alanine 118).

The cDNA sequence for the H8 antibody light chain (SEQ ID NO:12) was obtained from the amino acid sequences of a leader sequence (SEQ ID NO:1), the light chain variable region of the H8 antibody (SEQ ID NO:11, Kabat numbering), and the human κ Ig light chain constant region (SEQ ID NO:6, sequential numbering).

The cDNA sequence for the heavy chain of natalizumab (SEQ ID NO:16) was obtained from the amino acid sequences of a leader sequence (SEQ ID NO:13), the heavy chain variable region of natalizumab (SEQ ID NO:14, Kabat numbering) and the human IgG4 heavy chain constant region (SEQ ID NO:15, sequential numbering, Eu numbering starting at alanine 118; having a proline residue at position 225 and a cysteine residue at position 375).

The cDNA sequence for the natalizumab light chain (SEQ ID NO:19) was obtained from the amino acid sequences of a leader sequence (SEQ ID NO:17), the light chain variable region of natalizumab (SEQ ID NO:18, Kabat numbering), and the human κ Ig light chain constant region (SEQ ID NO:6, sequential numbering).

The heavy chain and light chain cDNA constructs were chemically synthesized by and obtained from a commercial source (Life Technologies). Cleavage of the leader sequence corresponded to the predicted cleavage site using the SignalP program (www.cbs.dtu.dk/services/SignalP/).

1b) Vector Construction and Cloning Strategy
For expression of the antibody chains the mammalian expression vector 0098 was constructed as follows. The CMV:BGHpA expression cassette was excised from the pcDNA3.1(-) (Life Technologies) plasmid and re-inserted back into the same original vector (still containing an intact CMV:BGHpA expression cassette), thereby duplicating the CMV:BGHpA expression cassette, to allow expression of both HC and LC cDNAs from a single plasmid vector. Subsequently, an IRES-DHFR fragment was isolated from the vector pOptiVEC-TOPO (Life Technologies) and inserted between the CMV promoter and the BGHpA polyadenylation sequence in one of the CMV:BGHpA expression cassettes.

The cDNAs for the heavy chain (HC) and the light chain (LC) were ligated into pMA-RQ and pMA-T plasmid vectors (Life Technologies), respectively, using SfiI restriction sites. After transfer to *E. coli* K12 and expansion, the LC cDNA was transferred to the mammalian expression vector 0098 using AscI and HpaI restriction sites. The resulting vector was digested with BamHI and NheI restriction enzymes, and ligated with the HC cDNA fragment, digested with the same restriction enzymes. The final vector, containing both the HC and LC expression cassettes (CMV:HC:BGHpA and CMV:LC-BGHpA, respectively) was transferred to and expanded in E. coli NEB 5-alpha cells (New England Biolabs).

Large-scale production of the final antibody mutant expression vector for transfection was performed using Maxi- or Megaprep kits (Qiagen).

2) Transient Expression in Mammalian Cells

Commercially available Expi293F cells (Life Technologies) were transfected with the antibody mutant expression vector prepared under 1) above using the ExpiFectamine transfection agent (Life Technologies) according to the manufacturer's instructions as follows: 75×10$^7$ cells were seeded in 300 mL Expi293 Expression medium; 300 µg of the antibody mutant expression vector was combined with 800 µl of ExpiFectamine transfection agent and added to the cells. One day after transfection, 1.5 mL Enhancer 1 and 15 mL Enhancer 2 were added to the culture. Six days post transfection, the cell culture supernatant was harvested by centrifugation at 4,000 g for 15 minutes and filtering the clarified harvest over MF 75 filters (Nalgene).

3) Purification of Expressed Proteins

Clarified harvests were first checked on expression level using SDS-PAGE electrophoresis. As production was deemed adequate, the antibodies were purified using commercially available protein A resin (MabSelect SuRe, GE Healthcare), using Äkta chromatographic equipment (GE Healthcare). A 20 cm bed height column was used with a maximum load of 25 mg/mL packed resin. The process was performed at RT.

After equilibration (PBS pH7.4) and loading the purification step employed two wash steps (PBS pH7.4 and NaAc pH5, respectively) and an elution step (25 mM NaAc, pH3) followed by a regeneration, rinse and cleaning step, respectively, before a new cycle was started. During the elution step the target protein was collected in a peak starting and stopping at an absorbance of 0.05-0.1 AU (0.2 cm cell length). After purification the protein was stored at −20° C. to −80° C.

4) Concentration and Buffer Exchange to the ADC Conjugation Buffer

Protein A eluates were, if needed, concentrated to 20-25 mg/mL using Vivaspin centrifugal devices (5 or 30 kDa cut-off, Vivaproducts). After obtaining the desired concentrations the concentrated solutions (typically 25 mg/mL) were dialyzed twice using PD10 columns (GE Healthcare) and 4.2 mM L-Histidine+50 mM Trehalose pH6.0 buffer. Alternatively, when protein A eluate concentrations were approximately 10 mg/mL, no concentration step was employed and the eluate was immediately dialyzed three times using snakeskin dialysis tube (10 kDa cut-off, Thermo Scientific) against 4.2 mM L-Histidine+50 mM Trehalose pH6.0 buffer. Any precipitate that appeared was removed by filtration after dialysis was completed. Concentrations were measured by UV spectroscopy using either Nanodrop or a cuvette UV spectrophotometer (both Thermo Scientific). Quality analysis showed that the protein had a purity of >95% and contained negligible amounts of dimers or fragments as determined by HPSEC. The isoelectric point of the engineered cysteine mutant was identical to the wild-type.

Using the similar/same procedure as described hereinabove for the preparation and purification of the engineered cysteine (VH 41C, Kabat numbering) anti-PSMA antibody, the engineered H8-HC41 (VH 41C, Kabat numbering) and the engineered cysteine natalizumab (CH 225P, 375C, Kabat numbering) antibodies, also the other antibodies of the examples were prepared and purified.

General Site-Specific Conjugation Protocol

To a solution of cysteine engineered antibody (5-10 mg/ml in 4.2 mM histidine, 50 mM trehalose, pH 6) EDTA (25 mM in water, 4% v/v) was added. The pH was adjusted to ~7.4 using TRIS (1 M in water, pH 8) after which TCEP (10 mM in water, 20 equivalents) was added and the resulting mixture was incubated at room temperature for 1-3 hrs. The excess TCEP was removed by either a PD-10 desalting column or a Vivaspin centrifugal concentrator (30 kDa cut-off, PES) using 4.2 mM histidine, 50 mM trehalose, pH 6. The pH of the resulting antibody solution was raised to ~7.4 using TRIS (1 M in water, pH 8) after which dehydroascorbic acid (10 mM in water, 20 equivalents) was added and the resulting mixture was incubated at room temperature for 1-2 hrs. DMA was added followed by a solution of linker drug (10 mM in DMA). The final concentration of DMA was 5-10%. The resulting mixture was incubated at room temperature in the absence of light for 1-16 hrs. In order to remove the excess of linker drug, activated charcoal was added and the mixture was incubated at room temperature for 1 hr. The coal was removed using a 0.2 µm PES filter and the resulting ADC was formulated in 4.2 mM histidine, 50 mM trehalose, pH 6 using a Vivaspin centrifugal concentrator (30 kDa cut-off, PES). Finally, the ADC solution was sterile filtered using a 0.22 µm PES filter.

General Conjugation Protocol for Conjugation Via Partially Reduced Endogenous Disulfides (Wt Conjugation)

To a solution of antibody (5-10 mg/ml in 4.2 mM histidine, 50 mM trehalose, pH 6) EDTA (25 mM in water, 4% v/v) was added. The pH was adjusted to ~7.4 using TRIS (1 M in water, pH 8) after which TCEP (10 mM in water, 1-3 equivalents depending on the antibody and the desired DAR) was added and the resulting mixture was incubated at room temperature for 1-3 hrs. DMA was added followed by a solution of linker drug (10 mM in DMA). The final concentration of DMA was 5-10%. The resulting mixture was incubated at room temperature in the absence of light for 1-16 hrs. In order to remove the excess of linker drug, activated charcoal was added and the mixture was incubated at room temperature for 1 hr. The coal was removed using a 0.2 µm PES filter and the resulting ADC was formulated in 4.2 mM histidine, 50 mM trehalose, pH 6 using a Vivaspin centrifugal concentrator (30 kDa cut-off, PES). Finally, the ADC solution was sterile filtered using a 0.22 µm PES filter.

Using the above general procedures, cysteine engineered and wild-type ADCs based on vc-seco-DUBA (SYD980; i.e., compound 18b, n=1 in Example 10 on page 209 of WO2011/133039), vc-MMAE and mc-MMAF linker drugs were synthesized and characterized using analytical Hydrophobic Interaction Chromatography (HIC), Size Exclusion Chromatography (SEC), Shielded Hydrophobic Phase Chromatography (SHPC), RP-HPLC and LAL endotoxin-testing.

For analytical HIC, 5-10 µL of sample (1 mg/ml) was injected onto a TSKgel Butyl-NPR column (4.6 mm ID×3.5 cm L, Tosoh Bioscience, cat. nr. 14947). The elution method consisted of a linear gradient from 100% Buffer A (25 mM sodium phosphate, 1.5 M ammonium sulphate, pH 6.95) to 100% of Buffer B (25 mM sodium phosphate, pH 6.95, 20% isopropanol) at 0.4 ml/min over 20 minutes. A Waters Acquity H-Class UPLC system equipped with PDA-detector and Empower software was used. Absorbance was measured at 214 nm and the retention time of ADCs was determined. As made apparent by analytical HIC, there were differences in the retention times (RTs) for the DAR2 species of the different cysteine engineered ADCs versus the wt conjugates (Tables 1, 2 and 3). Most interestingly, conjugating the linker drug at specific sites inside the Fab cavity or Fc cavity (as predicted by the molecular modelling algorithm) gave rise to a (dramatic) decrease in the retention time as compared to the ADCs that were conjugated via partially reduced endogenous disulfides, leading the present inventors to conclude that based on the HIC data, the engineered ADCs in which the linker drug is conjugated to specific sites in the Fab or Fc cavity are less hydrophobic than the wt conjugates. To further quantify this effect, the term relative hydrophobicity is introduced, which is defined as:

$$(RT_{DAR2} - RT_{DAR0})/(RT_{DAR2,wt\text{-}ADC} - RT_{DAR0,wt\text{-}ADC}).$$

In essence, the relative hydrophobicity is a measure that allows a facile comparison between the hydrophobicity of the engineered ADCs versus the wt-conjugated counterparts based on HIC data. The data are summarized in Tables 1, 2 and 3.

TABLE 1

The relative hydrophobicity of vc-seco-DUBA ADCs on the previously specified analytical HIC column:

| ADC (vc-seco-DUBA) | Cys mutations HC | Cys mutations LC | DAR | HMW (%)[2] | $RT_{DAR2}$ | $RT_{DAR0}$ | Relative hydrophobicity[3] |
|---|---|---|---|---|---|---|---|
| ADC-wt (SYD998)[1] | wt | wt | 1.8 | 7.7 | 9.7 | 6.9 | 1.0 |
| ADC-HC41 (SYD1091) | S41C | wt | 1.7 | 1.4 | 8.5 | 6.8 | 0.6 |
| ADC-HC120 (SYD1035)[6] | T120C | wt | 1.8 | 0.9 | 11.3 | 6.8 | 1.6 |
| ADC-HC152 | E152C | wt | 1.5 | 1.2 | 8.5 | 6.5 | 0.7 |
| ADC-HC153 | P153C | wt | 1.5 | 2.4 | 8.7 | 6.5 | 0.8 |
| ADC-HC236[6] | G236C | wt | 1.0 | 1.1 | 10.4 | 6.5 | 1.4 |
| ADC-HC247 | P247C | wt | 1.3 | 1.3 | 9.2 | 7.3 | 0.7 |
| ADC-HC339 | A339C | wt | 1.7 | 0.5 | 8.6 | 7.3 | 0.5 |
| ADC-HC375 | S375C | wt | 1.8 | 1.0 | 7.5 | 6.6 | 0.3 |
| ADC-HC376 | D376C | wt | 1.4 | 3.1 | 9.8 | 6.6 | 1.1 |
| ADC-HC41-120[7] | S41C, T120C | wt | 3.3 | 40.0 | 12.3 | 7.3 | 0.9 |
| ADC-HC41-375 | S41C, S375C | wt | 3.0-4.3[4] | 1.9 | 9.35 | 7.3 | 0.4 |
| ADC-LC40 | wt | P40C | 1.8 | 0.5 | 9.5 | 6.9 | 0.9 |
| ADC-LC41 | wt | G41C | 1.8 | 0.6 | 8.7 | 6.9 | 0.6 |
| ADC-LC109[6] | wt | T109C | 1.0 | — | 12.4 | 7.2 | 1.9 |
| ADC-LC154[6] | wt | L154C | 1.7 | 6.4 | 12.4 | 6.8 | 2.0 |
| ADC-LC157[6] | wt | G157C | 1.1 | — | 12.5 | 7.1 | 1.9 |
| ADC-LC165 | wt | E165C | 1.5 | 2.3 | 8.4 | 6.6 | 0.6 |
| ADC-LC205[6] | wt | V205C | 1.8 | 1.0 | 10.6 | 6.9 | 1.3 |
| H8-wt[1] | wt | wt | 2.0 | 4.4 | 9.9 | 6.4 | 1.0 |
| H8-HC40 | S40C | wt | 1.7 | 1.2 | 8.8 | 6.2 | 0.7 |
| H8-HC41 | P41C | wt | 1.7 | 0.4 | 7.4 | 6.2 | 0.3 |
| Natalizumab-HC375 | S375C[8] | wt | 1.7 | 26.0 | 7.8 | 6.8 | 0.4 |

[1]Random-non-site specific-attachment
[2]HMW are high molecular weight species, reflecting the amount of aggregates formed
[3]Defined as $(RT_{DAR2}-RT_{DAR0})/(RT_{DAR2,\,wt\text{-}ADC}-RT_{DAR0,\,wt\text{-}ADC})$, RT is retention time
[4]Based on MS-data
[5]RT, wt DAR4 species = 12.2
[6]Comparator ADCs with linker drug conjugated to a cysteine residue pointing outwards
[7]ADC with linker drug conjugated to one cysteine in the Fab cavity and one cysteine residue pointing outwards; process not yet optimised
[8]Also 225P mutation to prevent dimerisation of IgG4

TABLE 2

The relative hydrophobicity of vc-MMAE ADCs on the previously specified analytical HIC column:

| ADC-wt MMAE | Cys mutations HC | Cys mutations LC | DAR | HMW (%)[1] | $RT_{DAR2}$ | $RT_{DAR0}$ | Relative hydrophobicity[2] |
|---|---|---|---|---|---|---|---|
| ADC-wt | wt | wt | 1.7 | 0.6 | 9.6 | 7.2 | 1.0 |
| ADC-HC41 | S41C | wt | 1.8 | 0.5 | 8.1 | 7.2 | 0.4 |
| ADC-LC40 | wt | P40C | 1.8 | 0.6 | 8.5 | 7.2 | 0.5 |
| ADC-LC41 | wt | G41C | 1.9 | 0.9 | 8.4 | 7.3 | 0.5 |
| H8-HC40 | S40C | wt | 1.7 | 1.4 | 8.1 | 6.5 | ND[3] |

1 HMW are high molecular weight species, reflecting the amount of aggregates formed
2 Defined as $(RT_{DAR2}-RT_{DAR0})/(RT_{DAR2,\,wt\text{-}ADC}-RT_{DAR0,\,wt\text{-}ADC})$, RT is retention time
3 ND is not determined; wild-type H8-vc-MMAE was not prepared

TABLE 3

The relative hydrophobicity of mc-MMAF ADCs on the previously specified analytical HIC column:

| ADC-wt (MMAF) | Cys mutations HC | Cys mutations LC | DAR | HMW (%)[1] | $RT_{DAR2}$ | $RT_{DAR0}$ | Relative hydrophobicity[2] |
|---|---|---|---|---|---|---|---|
| ADC-wt | wt | wt | 1.8 | 0.6 | 8.0 | 7.2 | 1.0 |
| ADC-HC41 | S41C | wt | 1.8 | 0.5 | 7.4 | 7.2 | 0.3 |
| ADC-LC40 | wt | P40C | 1.8 | 0.5 | 7.6 | 7.2 | 0.5 |
| ADC-LC41 | wt | G41C | 1.8 | 0.6 | 7.5 | 7.3 | 0.3 |
| H8-wt | wt | wt | 4.2 | 0.4 | 7.2 | 6.2 | 1.0 |
| H8-HC40 | S40C | wt | 1.4 | 1.2 | 6.9 | 6.5 | 0.4 |

[1] HMW are high molecular weight species, reflecting the amount of aggregates formed
[2] Defined as $(RT_{DAR2}-RT_{DAR0})/(RT_{DAR2, wt-ADC}-RT_{DAR0, wt-ADC})$, RT is retention time Cellular Binding Three anti-PSMA ADCs SYD998 (wt), SYD1091 (HC41) and comparator SYD1035 (HC120) had equal binding affinities on PSMA-expressing LNCaP-C4.2 cells ($EC_{50}$ in the range of 0.1-0.2 μg/ml) similar to the wild-type antibody, and all three ADCs were unable to bind to PSMA-negative DU-145 cells ($EC_{50}$>10 μg/ml).

Two anti-5T4 ADCs H8-wt and H8-HC40 had equal binding affinities on 5T4-expressing MDA-MB-468 cells ($EC_{50}$ in the range of 0.1-1.2 μg/ml) similar to the wild-type H8 antibody, and both ADCs were unable to bind to 5T4-negative SK-MEL-30 cells ($EC_{50}$>10 μg/ml).

The antigen binding properties of the ADCs were thus unaffected by the attached duocarmycin derivative linker drug.

In Vitro Cytotoxicity

The potencies of the site-specifically conjugated anti-PSMA ADCs were similar to the conventionally linked wild-type ADC (SYD998) on PSMA-expressing LNCaP-C4.2 cells ($IC_{50}$ in the range of 0.1-0.5 nM, based on drug equivalents, see Table 4 below). All ADCs were inactive on PSMA-negative DU-145 cells ($IC_{50}$>70 nM) indicating selective killing of tumour cells through PSMA.

The two non-binding control ADCs were at least 50-times less potent than the anti-PSMA ADCs on each of the cell lines evaluated.

TABLE 4

In vitro cytotoxicity of the anti-PSMA-vc-seco-DUBA ADCs in human tumour cells expressing PSMA

| ADC (ve-seco-DUBA) | Cys mutations HC | Cys mutations LC | PSMA-positive cell line LNCaP-C4.2 $IC_{50}$ (nM) | 95% CI (nM)[1] | % efficacy[2] |
|---|---|---|---|---|---|
| ADC-wt (SYD998) | wt | wt | 0.23 | 0.20-0.27 | 82 |
| ADC-HC41 (SYD1091) | S41C | wt | 0.25 | 0.21-0.28 | 78 |
| ADC-HC120 (SYD1035) | T120C | wt | 0.14 | 0.13-0.16 | 82 |
| ADC-HC152 | E152C | wt | 0.44 | 0.36-0.55 | 78 |
| ADC-HC153 | P153C | wt | 0.34 | 0.28-0.41 | 79 |
| ADC-HC236 | G236C | wt | 0.22 | 0.19-0.26 | 76 |
| ADC-HC247 | P247C | wt | 0.10 | 0.09-0.12 | 82 |
| ADC-HC339 | A339C | wt | 0.12 | 0.11-0.13 | 83 |
| ADC-HC375 | S375C | wt | 0.25 | 0.22-0.28 | 81 |
| ADC-HC376 | D376C | wt | 0.20 | 0.18-0.22 | 82 |
| ADC-LC40 | wt | P40C | 0.30 | 0.23-0.37 | 80 |
| ADC-LC41 | wt | G41C | 0.31 | 0.25-0.38 | 80 |
| ADC-LC154 | wt | L154C | 0.24 | 0.19-0.29 | 82 |
| ADC-LC165 | wt | E165C | 0.51 | 0.40-0.65 | 79 |
| ADC-LC205 | wt | V205C | 0.17 | 0.15-0.19 | 83 |
| Non-binding control-wt | wt | wt | 28.86 | 24.76-36.02 | 96 |
| Non-binding control-HC41 | P41C | wt | >100 | n.a. | n.a. |
| Free linker drug | | | 0.02 | 0.02-0.03 | 98 |

[1] 95% CI is 95% confidence interval
[2] Percentage efficacy was given at the highest concentration tested (~100 nM) and calculated by dividing the measured luminescence for each drug or ADC with the average mean of untreated cells (only growth medium) multiplied by 100.

Conjugation of vc-MMAE to the HC41, LC40 and LC41 positions on anti-PSMA antibodies resulted in cytotoxic potencies in PSMA-positive LNCaP-C4.2 cells similar to anti-PSMA-vc-seco-DUBA linked on these cysteine sites (Tables 4 and 5). The anti-PSMA-vc-MMAE ADCs lacked activity on PSMA-negative DU-145 cells ($IC_{50}$>70 nM).

TABLE 5

In vitro cytotoxicity of the anti-PSMA-vc-MMAE ADCs in human tumour cells expressing PSMA

| ADC (ve-MMAE) | Cys mutations HC | Cys mutations LC | PSMA-positive cell line LNCaP-C4.2 $IC_{50}$ (nM) | 95% CI (nM)[1] | % efficacy[2] |
|---|---|---|---|---|---|
| ADC-wt | wt | wt | 0.34 | 0.31-0.38 | 89 |
| ADC-HC41 | S41C | wt | 0.39 | 0.35-0.43 | 91 |
| ADC-LC40 | wt | P40C | 0.31 | 0.27-0.35 | 90 |
| ADC-LC41 | wt | G41 C | 0.33 | 0.29-0.37 | 90 |
| Non-binding control-wt | wt | wt | >100 | n.a. | 90 |
| Free linker drug | | | 0.23 | 0.18-0.28 | 94 |

[1] 95% CI is 95% confidence interval
[2] Percentage efficacy was given at the highest concentration tested (~100 nM) and calculated by dividing the measured luminescence for each drug or ADC with the average mean of untreated cells (only growth medium) multiplied by 100.

The potencies of the engineered anti-5T4 ADCs were equal to the conventionally linked ADC H8-wt on 5T4-expressing MDA-MB-468 cells ($IC_{50}$ between 0.07 and 0.09 nM, Table 6). The anti-5T4 ADCs were inactive on 5T4-negative SK-MEL-30 cells ($IC_{50}$>90 nM).

TABLE 6

In vitro cytotoxicity of the anti-5T4-vc-seco-DUBA ADCs in human tumour cells expressing 5T4

| ADC (vc-seco-DUBA) | Cys mutations HC | Cys mutations LC | vc-seco-DUBA 5T4-positive cell line MDA-MB-468 $IC_{50}$ (nM) | 95% CI (nM)[1] | % efficacy[2] |
|---|---|---|---|---|---|
| H8-wt | wt | wt | 0.09 | 0.08-0.10 | 91 |
| H8-HC40 | S40C | wt | 0.07 | 0.07-0.08 | 88 |
| H8-HC41 | P41C | wt | 0.07 | 0.06-0.08 | 88 |
| Non-binding control-HC41 | P41C | wt | 40.18 | 34.24-47.16 | 85 |
| Free linker drug | | | 0.02 | 0.01-0.02 | 94 |

[1]95% CI is 95% confidence interval
[2]Percentage efficacy was given at the highest concentration tested (~100 nM) and calculated by dividing the measured luminescence for each drug or ADC with the average mean of untreated cells (only growth medium) multiplied by 100.

Together, these data show that the tested cysteine positions for site-specific conjugation did not have an impact on the tumour cell killing potency of ADCs comprising two different linker drugs. Moreover, site-specific linkage of linker drugs in the variable region of the Fab part of different antibodies is generally applicable.

Enzymatic Cleavage by Cathepsin B

The valine-citrulline moiety present in the linker of the ADCs with vc-seco-DUBA (SYD980) and vc-MMAE can be cleaved by cysteine proteases, such as cathepsin B, which results in subsequent intracellular release of the (seco-)DUBA or MMAE drug inside the tumour lysosomes or extracellular in the tumour microenvironment. To assess the sensitivity towards cathepsin B, the ADCs were treated for 2 minutes and 4 hours with activated cathepsin B (Calbiochem). The cytotoxic activity of the released drug from the anti-PSMA ADCs was measured on PSMA-negative DU-145 cells. The cytotoxic activity of the released drug from the anti-5T4 ADCs was measured on 5T4-negative SK-MEL-30 cells. During the pre-incubation step at 37° C., 1 mg/ml of each ADC was mixed with 5 μg/ml cathepsin B (0.04 units/well) in 0.1M Na-acetate pH 5 containing 4 mM DTT. As a control, 1 mg/ml of each ADC was directly diluted in culture medium (RPMI 1640, 10% qualified FBS). Serial dilutions were made from these ADC solutions in culture medium. To measure release of the respective free toxins DUBA or MMAE, PSMA-negative DU-145 cells (1,000 cells/well) and 5T4-negative SK-MEL-30 cells (2,000 cells/well) were cultured with the ADCs for 6 days, and the cell viability was measured after 6 days using the CellTiter-Glo™ (CTG) assay kit.

Differences in potency of the released drug on PSMA-negative DU-145 cells and 5T4-negative SK-MEL-30 cells reflect the amount of drug that is cleaved from the ADC, and thereby the accessibility of the valine-citrulline cleavage site for cathepsin B. As shown in Table 7, the sensitivity for proteolytic cleavage differed amongst the ADCs after four hours of exposure to activated cathepsin B (see $IC_{50}$ values), while none of the ADCs were cleaved after a short period of 2 minutes exposure with cathepsin B ($IC_{50}$>10 nM, data not shown in Table).

Together these data show that the site of conjugation influences the accessibility of the linker drug for enzymatic cleavage, and that the vc-seco-DUBA (SYD980) linker drug in the anti-PSMA ADCs ADC-HC41, ADC-HC152, ADC-HC339, ADC-HC375, ADC-LC41, and ADC-LC165 are most shielded from cleavage by said enzyme. Conjugation of vc-MMAE to the HC41 and LC41 positions of the anti-PSMA antibodies resulted in similar shielding of the valine-citrulline cleavage site (Table 7). A similar trend was also seen for the anti-5T4 antibody H8-HC41 conjugated to vc-seco-DUBA (SYD980) via the same HC41 position.

These data together show that particularly the 41C position is a suitable position for site-specific conjugation of linker-drugs to various antibodies.

TABLE 7

Cytotoxicity of the free drug cleaved by cathepsin B

| ADC | Cys mutations HC | Cys mutations LC | 4 hours pre-incubation with cathepsin B $IC_{50}$ (nM) | 95% CI (nM) | % efficacy |
|---|---|---|---|---|---|
| anti-PSMA antibodies conjugated to vc-seco-DUBA | | | | | |
| ADC-wt (SYD998) | wt | wt | 0.70 | 0.62-0.79 | 97 |
| ADC-HC41 (SYD1091) | S41C | wt | ~5.00 | n.a. | 59 |
| ADC-HC120 (SYD1035) | T120C | wt | 0.38 | 0.34-0.42 | 96 |
| ADC-HC152 | E152C | wt | >10 | n.a. | 50 |
| ADC-HC153 | P153C | wt | 0.76 | 0.69-0.84 | 98 |
| ADC-HC236 | G236C | wt | 2.08 | 1.64-2.65 | 100 |
| ADC-HC247 | P247C | wt | 2.01 | 1.69-2.39 | 99 |
| ADC-HC339 | A339C | wt | 5.00 | 3.50-7.15 | 99 |
| ADC-HC375 | S375C | wt | >10 | n.a. | 45 |
| ADC-HC376 | D376C | wt | 0.60 | 0.52-0.68 | 98 |
| ADC-LC40 | wt | P40C | 2.11 | 1.91-2.34 | 96 |
| ADC-LC41 | wt | G41C | >10 | n.a. | n.a. |
| ADC-LC154 | wt | L154C | 0.26 | 0.22-0.30 | 98 |
| ADC-LC165 | wt | E165C | >10 | n.a. | 50 |
| ADC-LC205 | wt | V205C | 0.48 | 0.41-0.58 | 97 |
| Non-binding control-wt | wt | wt | 0.32 | 0.28-0.35 | 97 |
| Non-binding control-HC41 | P41C | wt | 1.56 | 1.36-1.79 | 98 |
| anti-PSMA antibodies conjugated to vc-MMAE | | | | | |
| ADC-wt | wt | wt | 0.63 | 0.31-0.38 | 96 |
| ADC-HC41 | S41C | wt | 2.28 | 2.11-2.46 | 97 |
| ADC-LC40 | wt | P40C | 0.60 | 0.55-0.64 | 96 |
| ADC-LC41 | wt | G41C | 4.28 | 3.65-5.02 | 96 |
| Non-binding control-wt | wt | wt | 0.64 | 0.57-0.72 | 97 |
| anti-5T4 antibodies conjugated to vc-seco-DUBA | | | | | |
| H8-wt | wt | wt | 0.35* | 0.30-0.40 | 98 |
| H8-HC40 | S40C | wt | 0.98 | 0.83-1.15 | 93 |
| H8-HC41 | P41C | wt | 1.27* | 0.98-1.67 | 98 |
| Non-binding control-HC41 | P41C | wt | 1.86 | 1.42-2.45 | 85 |

*LNCaP-C4.2 was used as the 5T4-negative cell line.

Tumour Xenograft Animal Model

The in vivo efficacy of three anti-PSMA ADCs was evaluated in the LNCaP C4-2 prostate cancer xenograft model. The LnCaP-C4.2 cell line is a human prostate carcinoma epithelial cell line derived from a xenograft that was serially propagated in mice after castration-induced regression and relapse of the parental, androgen-dependent LnCaP-FGC xenograft cell line.

Tumours were induced subcutaneously by injecting $1 \times 10^7$ of LnCap C4.2 cells in 200 μL of RPMI 1640 containing matrigel (50:50, v:v) into the right flank of male CB17-SCID mice. LnCaP-C4.2 tumour cell implantation was performed 24 to 72 hours after a whole body irradiation with a γ-source (1.44 Gy, $^{60}$Co, BioMep, Bretenières, France). Treatments were started when the tumours reached a mean volume of 100-200 mm³. Mice were randomized according to their individual tumour volume into groups and received a single i.v. injection of anti-PSMA ADC (2 or 10 mg/kg) or vehicle in the tail vein. Changes in tumour volumes (FIG. 2) and body weight (FIG. 3) were monitored. All three ADCs have an average DAR of approximately 1.8.

Figure 2A:
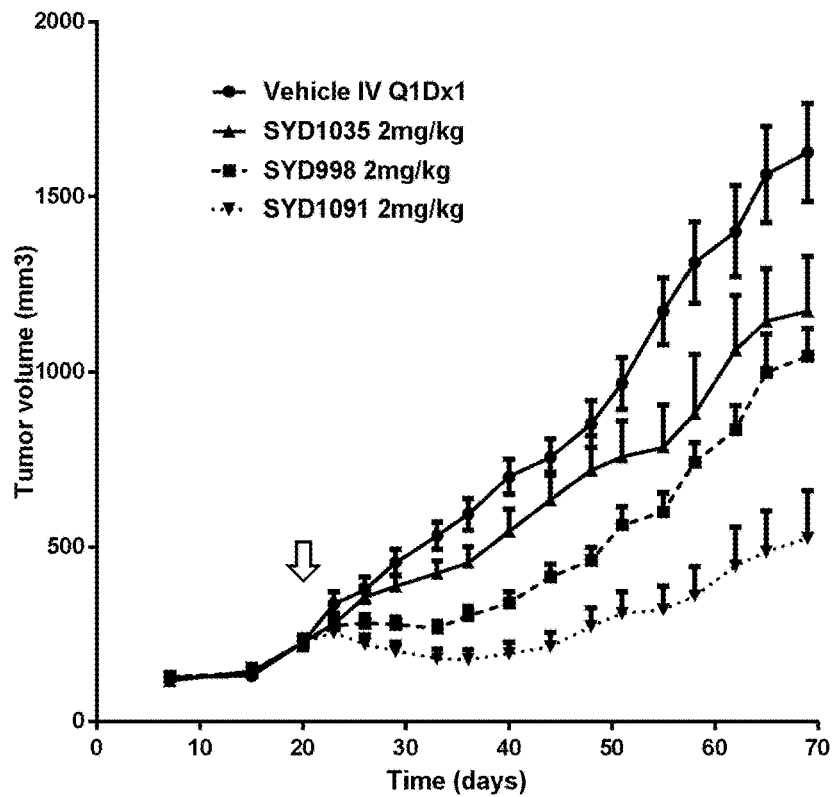
FIG. 2B. In vivo efficacy of engineered cysteine anti-PSMA (VH S41C) ADC (SYD1091) versus vehicle control, comparator engineered cysteine anti-PSMA (CH T120C) ADC (SYD1035), and non-engineered anti-PSMA wt ADC (SYD998) at 10 mg/kg each.
Figure 2B:
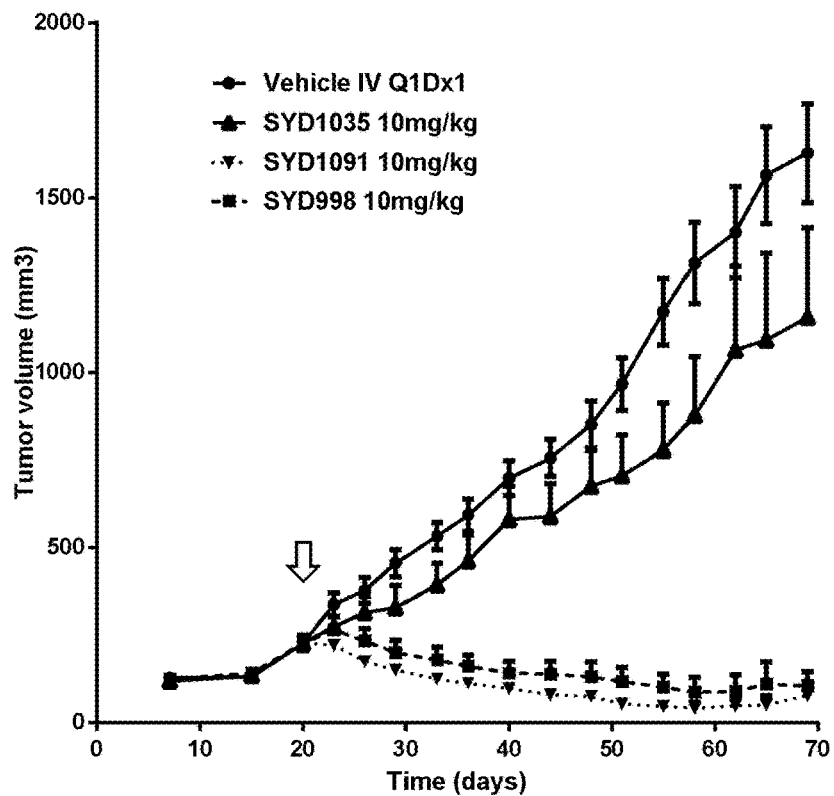
Figure 3:
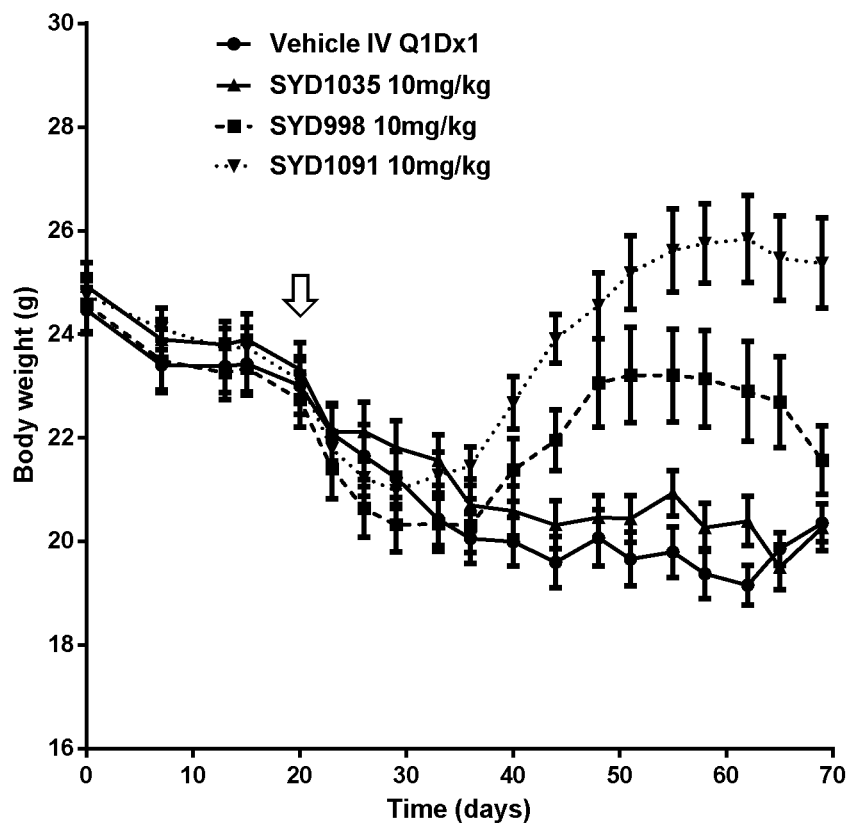
FIG. 3. Effect on body weight of engineered cysteine anti-PSMA (VH S41C) ADC (SYD1091) versus vehicle control, comparator engineered cysteine anti-PSMA (CH T120C) ADC (SYD1035), and non-engineered anti-PSMA wt ADC (SYD998) at 10 mg/kg each.

FIG. 2A demonstrates that at 2 mg/kg the comparator engineered cysteine anti-PSMA ADC SYD1035 is less active compared to the native, non-engineered cysteine SYD998. However, the efficacy of SYD1091, an engineered cysteine ADC in accordance with the present invention, is significantly better than the comparator SYD1035 and is better than the native, non-engineered SYD998. The difference between the comparator SYD1035 and SYD1091 is even more pronounced at 10 mg/kg as shown in FIG. 2B. Mice bearing LnCap C4.2 tumours develop cachexia as illustrated in FIG. 3. This loss of body weight is often restored after administration of efficacious treatments and is considered a sensitive efficacy biomarker. Treatment with SYD1091 resulted in much faster restoration of the body weights than was seen with the comparator SYD1035 or native, non-engineered SYD998 (FIG. 3).

The in vivo efficacy of two anti-5T4 ADCs, i.e. the native H8-vc-seco-DUBA (average DAR 2.0) and the engineered cysteine (VH P41C) ADC H8-41C-vc-seco-DUBA (average DAR 1.7), was evaluated in the PA-1 ovarian cancer xenograft model. The PA-1 cell line was established from cells taken from ascitic fluid collected from a woman with ovarian carcinoma (Zeuthen J. et al. Int. J. Cancer 1980; 25(1): 19-32).

Figure 4A:
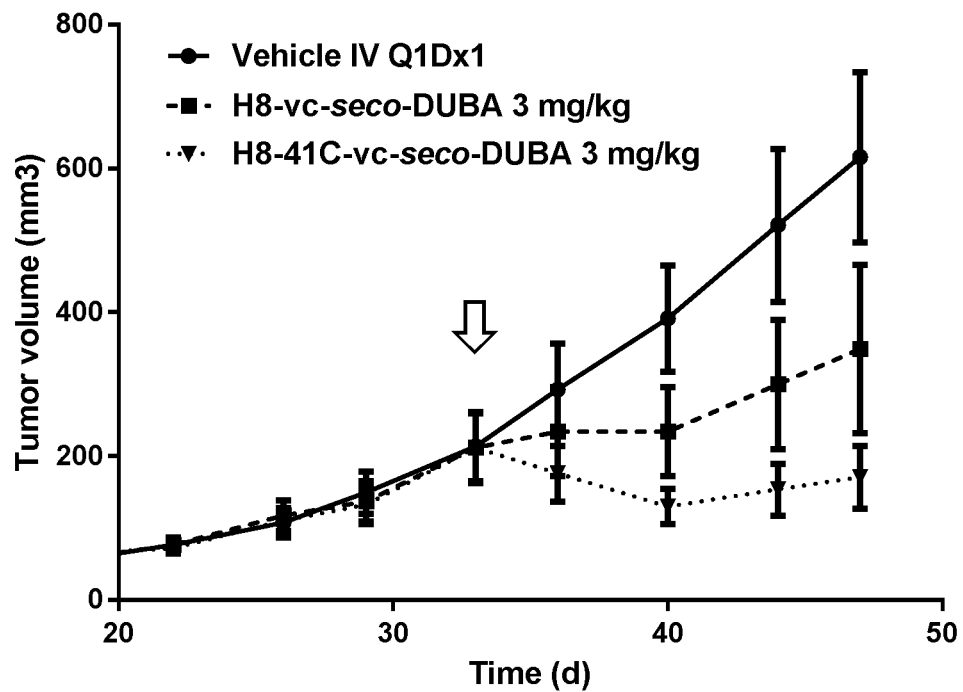
FIG. 4A. In vivo efficacy of engineered cysteine anti-5T4 (VH P41C) H8 ADC (H8-41C-vc-seco-DUBA) versus vehicle control, and non-engineered anti-5T4 wt H8 ADC (H8-vc-seco-DUBA) at 3 mg/kg each.
Figure 4B:
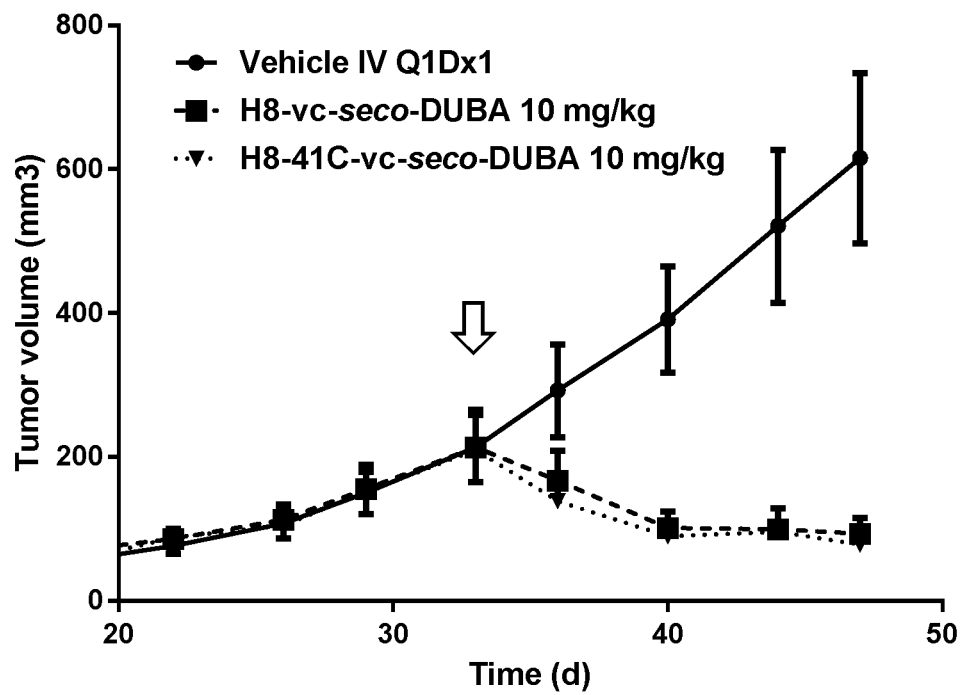
FIG. 4B. In vivo efficacy of engineered cysteine anti-5T4 (VH P41C) H8 ADC (H8-41C-vc-seco-DUBA) versus vehicle control, and non-engineered anti-5T4 wt H8 ADC (H8-vc-seco-DUBA) at 10 mg/kg each.

PA-1 tumours were induced subcutaneously by injecting $1 \times 10^7$ cells in 100 μL RPMI 1640 medium containing matrigel (50/50, v/v) into the right flank of female Balb/c nude mice. PA-1 tumour cell injection was performed 24 to 72 hours after a whole body irradiation with a γ-source (2 Gy, $^{60}$Co, BioMep, Bretenières, France). Treatments were started when the tumours reached a mean volume of 200-300 mm$^3$. Mice were randomized according to their individual tumour volume into groups and received a single i.v. injection of anti-5T4 ADC (3 or 10 mg/kg) or vehicle in the tail vein and changes in tumour volumes (FIGS. 4A and 4B) were monitored. Even though both variants have similar efficacy at the higher dose 10 mg/kg (FIG. 4B), at 3 mg/kg the engineered cysteine anti-5T4 ADC H8-41C-vc-seco-DUBA was clearly more active when compared to the native, non-engineered anti-5T4 ADC, H8-vc-seco-DUBA (FIG. 4A).

Together these findings demonstrate that, in vivo, the site-specific engineered cysteine ADCs according to the present invention show favourable properties with respect to the efficacy in mouse tumour models.

```
(HAVT20 leader sequence)
                                                              SEQ ID NO: 1
    1 MACPGFLWAL VISTCLEFSM A (anti-PSMA antibody HC S41C)
                                                              SEQ ID NO: 2
    1 EVQLVQSGAE VKKPGASVKI SCKTSGYTFT EYTIHWVKQA CGKGLEWIGN

51 INPNNGGTTY NQKFEDRATL TVDKSTSTAY MELSSLRSED TAVYYCAAGW

101 NFDYWGQGTT VTVSS (human IgG1 antibody HC constant region)
                                                              SEQ ID NO: 3
    1 ASTKGPSVFP LAPSSKSTSG GTAALGCLVK DYFPEPVTVS WNSGALTSGV

51 HTFPAVLQSS GLYSLSSVVT VPSSSLGTQT YICNVNHKPS NTKVDKKVEP

101 KSCDKTHTCP PCPAPELLGG PSVFLFPPKP KDTLMISRTP EVTCVVVDVS

151 HEDPEVKFNW YVDGVEVHNA KTKPREEQYN STYRVVSVLT VLHQDWLNGK

201 EYKCKVSNKA LPAPIEKTIS KAKGQPREPQ VYTLPPSRDE LTKNQVSLTC

281 LVKGFYPSDI AVEWESNGQP ENNYKTTPPV LDSDGSFFLY SKLTVDKSRW

301 QQGNVFSCSV MHEALHNHYT QKSLSLSPGK (anti-PSMA antibody HC S41C cDNA)
                                                              SEQ ID NO: 4
    1 ATGGCCTGTC CTGGATTTCT GTGGGCCCTC GTGATCAGCA CCTGTCTGGA ATTCAGCATG

51 GCCGAGGTGC AGCTGGTGCA GTCTGGCGCC GAAGTGAAGA AACCAGGCGC CAGCGTGAAG

121 ATCAGCTGCA AGACCAGCGG CTACACCTTC ACCGAGTACA CCATCCACTG GGTCAAGCAG

181 GCCTGTGGCA AGGGCCTGGA ATGGATCGGC AACATCAACC CAACAACGG CGGCACCACC

241 TACAACCAGA AGTTCGAGGA CCGGGCCACC CTGACCGTGG ACAAGAGCAC AAGCACCGCC

301 TACATGGAAC TGAGCAGCCT GCGGAGCGAG GACACCGCCG TGTACTATTG TGCCGCCGGA

361 TGGAACTTCG ACTACTGGGG CCAGGGCACC ACCGTGACAG TGTCTAGCGC CAGCACAAAG

421 GGCCCCAGCG TGTTCCCTCT GGCCCCTAGC AGCAAGTCTA CCTCTGGCGG AACAGCCGCC

481 CTGGGCTGCC TCGTGAAGGA CTACTTTCCC GAGCCCGTGA CCGTGTCCTG GAACTCTGGC

541 GCTCTGACAA GCGGCGTGCA CACCTTTCCA GCCGTGCTGC AGAGCAGCGG CCTGTACTCT
```

```
 601 CTGAGCAGCG TCGTGACTGT GCCCAGCAGC AGCCTGGGCA CCCAGACCTA CATCTGCAAC

661 GTGAACCACA AGCCCAGCAA CACCAAGGTG GACAAAAAGG TGGAACCCAA GAGCTGCGAC

721 AAGACCCACA CCTGTCCCCC TTGTCCTGCC CCTGAACTGC TGGGCGGACC TTCCGTGTTC

781 CTGTTCCCCC CAAAGCCCAA GGACACCCTG ATGATCAGCC GGACCCCCGA AGTGACCTGC

841 GTGGTGGTGG ATGTGTCCCA CGAGGACCCT GAAGTGAAGT TCAATTGGTA CGTGGACGGC

901 GTGGAAGTGC ACAACGCCAA GACCAAGCCC AGAGAGGAAC AGTACAACAG CACCTACCGG

961 GTGGTGTCCG TGCTGACAGT GCTGCACCAG GACTGGCTGA ACGGCAAAGA GTACAAGTGC

1021 AAGGTGTCCA ACAAGGCCCT GCCTGCCCCC ATCGAGAAAA CCATCAGCAA GGCCAAGGGC

1081 CAGCCCCGCG AACCCCAGGT GTACACACTG CCTCCCAGCA GGGACGAGCT GACCAAGAAC

1141 CAGGTGTCCC TGACATGCCT CGTGAAAGGC TTCTACCCCT CCGATATCGC CGTGGAATGG

1201 GAGAGCAACG GCCAGCCCGA GAACAACTAC AAGACCACCC CCCCTGTGCT GGACAGCGAC

1261 GGCTCATTCT TCCTGTACAG CAAGCTGACT GTGGATAAGT CCCGGTGGCA GCAGGGCAAC

1321 GTGTTCAGCT GCAGCGTGAT GCACGAGGCC CTGCACAACC ACTACACCCA GAAAAGCCTG

1381 TCCCTGAGCC CCGGCAAG (anti-PSMA antibody LC)
                                                         SEQ ID NO: 5
   1 DIVMTQSPSS LSASVGDRVT ITCKASQDVG TAVDWYQQKP GKAPKLLIYW

51 ASTRHTGVPD RFTGSGSGTD FTLTISSLQP EDFADYFCQQ YNSYPLTFGG

101 GTKLEIK (human IgG antibody LC κ constant region)
                                                         SEQ ID NO: 6
   1 RTVAAPSVFI FPPSDEQLKS GTASVVCLLN NFYPREAKVQ WKVDNALQSG

51 NSQESVTEQD SKDSTYSLSS TLTLSKADYE KHKVYACEVT HQGLSSPVTK

101 SFNRGEC (anti-PSMA antibody LC cDNA)
                                                         SEQ ID NO: 7
   1 ATGGCTTGTC CTGGATTTCT GTGGGCCCTC GTGATCAGCA CCTGTCTGGA ATTCAGCATG

61 GCCGACATCG TGATGACCCA GAGCCCCAGC TCTCTGAGCG CCAGCGTGGG CGACAGAGTG

121 ACCATCACAT GCAAGGCCAG CCAGGACGTG GGCACCGCCG TGGATTGGTA TCAGCAGAAG

181 CCTGGCAAGG CCCCCAAGCT GCTGATCTAC TGGGCCAGCA CCAGACACAC CGGCGTGCCC

241 GATAGATTCA CAGGCAGCGG CTCCGGCACC GACTTCACCC TGACAATCAG CAGCCTGCAG

301 CCCGAGGACT TCGCCGACTA CTTCTGCCAG CAGTACAACA GCTACCCCCT GACCTTCGGC

361 GGAGGCACCA AGCTGGAAAT CAAGCGGACA GTGGCCGCTC CCAGCGTGTT CATCTTCCCA

421 CCTAGCGACG AGCAGCTGAA GTCTGGCACC GCCTCTGTCG TGTGCCTGCT GAACAACTTC

481 TACCCCCGCG AGGCCAAGGT GCAGTGGAAG GTGGACAATG CCCTGCAGAG CGGCAACAGC

541 CAGGAAAGCG TGACCGAGCA GGACAGCAAG GACTCCACCT ACAGCCTGAG CAGCACCCTG

601 ACCCTGAGCA AGGCCGACTA CGAGAAGCAC AAGGTGTACG CCTGCGAAGT GACCCACCAG

661 GGCCTGTCTA GCCCCGTGAC CAAGAGCTTC AACCGGGGCG AGTGC (H8 HC P41C)
                                                         SEQ ID NO: 8
   1 QVQLVQSGAE VKKPGASVKV SCKASGYSFT GYYMHWVKQS CGQGLEWIGR

51 INPNNGVTLY NQKFKDRVTM TRDTSISTAY MELSRLRSDD TAVYYCARST

101 MITNYVMDYW GQGTLVTVSS
```

(human IgG1 antibody HC constant region)
SEQ ID NO: 9
```
  1 ASTKGPSVFP LAPSSKSTSG GTAALGCLVK DYFPEPVTVS WNSGALTSGV
 51 HTFPAVLQSS GLYSLSSVVT VPSSSLGTQT YICNVNHKPS NTKVDKKVEP
101 KSCDKTHTCP PCPAPELLGG PSVFLFPPKP KDTLMISRTP EVTCVVVDVS
151 HEDPEVKFNW YVDGVEVHNA KTKPREEQYN STYRVVSVLT VLHQDWLNGK
201 EYKCKVSNKA LPAPIEKTIS KAKGQPREPQ VYTLPPSREE MTKNQVSLTC
211 LVKGFYPSDI AVEWESNGQP ENNYKTTPPV LDSDGSFFLY SKLTVDKSRW
301 QQGNVFSCSV MHEALHNHYT QKSLSLSPGK
```

(H8 HC P41C cDNA)
SEQ ID NO: 10
```
   1 ATGGCCTGTC CTGGATTTCT GTGGGCCCTC GTGATCAGCA CCTGTCTGGA ATTCAGCATG
  61 GCCCAGGTGC AGCTGGTGCA GTCTGGCGCC GAAGTGAAGA AACCAGGCGC CAGCGTGAAG
 121 GTGTCCTGCA AGGCCAGCGG CTACAGCTTC ACCGGCTACT ACATGCACTG GGTCAAGCAG
 181 AGCTGCGGCC AGGGCCTGGA ATGGATCGGC AGAATCAACC CCAACAACGG CGTGACCCTG
 241 TACAACCAGA AATTCAAGGA CCGCGTGACC ATGACCCGGG ACACCAGCAT CAGCACCGCC
 301 TACATGGAAC TGAGCCGGCT GAGAAGCGAC GACACCGCCG TGTACTACTG CGCCCGGTCC
 361 ACCATGATCA CCAACTACGT GATGGACTAC TGGGGCCAGG GCACCCTCGT GACAGTGTCT
 431 AGCGCCAGCA CAAAGGGCCC CAGCGTGTTC CCTCTGGCCC CTAGCAGCAA GAGCACATCT
 431 GGCGGAACAG CCGCCCTGGG CTGCCTCGTG AAGGATTACT TCCCCGAGCC CGTGACCGTG
 541 TCCTGGAATA GCGGAGCCCT GACAAGCGGC GTGCACACCT TCCAGCCGT GCTGCAGAGC
 601 AGCGGCCTGT ACTCTCTGAG CAGCGTCGTG ACTGTGCCCA GCAGCAGCCT GGGCACCCAG
 661 ACCTACATCT GCAACGTGAA CCACAAGCCC AGCAACACCA AGGTGGACAA GAAGGTGGAA
 721 CCCAAGAGCT GCGACAAGAC CCACACCTGT CCCCCTTGTC CTGCCCCTGA ACTGCTGGGC
 781 GGACCTTCCG TGTTCCTGTT CCCCCCAAAG CCCAAGGACA CCCTGATGAT CAGCCGGACC
 841 CCCGAAGTGA CCTGCGTGGT GGTGGATGTG TCCCACGAGG ACCCTGAAGT GAAGTTCAAT
 901 TGGTACGTGG ACGGCGTGGA AGTGCACAAC GCCAAGACCA AGCCCAGAGA GGAACAGTAC
 961 AACAGCACCT ACCGGGTGGT GTCCGTGCTG ACAGTGCTGC ACCAGGACTG GCTGAACGGC
1021 AAAGAGTACA AGTGCAAGGT GTCCAACAAA GCCCTGCCTG CCCCCATCGA GAAAACCATC
1081 AGCAAGGCCA AGGGCCAGCC CCGCGAACCC CAGGTGTACA CACTGCCTCC CAGCCGGGAA
1141 GAGATGACCA AGAACCAGGT GTCCCTGACA TGCCTCGTGA AAGGCTTCTA CCCCTCCGAT
1201 ATCGCCGTGG AATGGGAGAG CAACGGCCAG CCCGAGAACA ACTACAAGAC CACCCCCCCT
1261 GTGCTGGACA GCGACGGCTC ATTCTTCCTG TACAGCAAGC TGACCGTGGA CAAGTCCCGG
1321 TGGCAGCAGG GCAACGTGTT CAGCTGCAGC GTGATGCACG AGGCCCTGCA CAACCACTAC
1381 ACCCAGAAGT CCCTGAGCCT GAGCCCCGGC AAA
```

(H8 LC)
SEQ ID NO: 11
```
  1 DIVMTQSPDS LAVSLGERAT INCKASQSVS NDVAWYQQKP GQSPKLLISY
 51 TSSRYAGVPD RFSGSGSGTD FTLTISSLQA EDVAVYFCQQ DYNSPPTFGG
101 GTKLEIK
```

(H8 LC cDNA)
SEQ ID NO: 12
```
  1 ATGGCCTGTC CTGGATTTCT GTGGGCCCTC GTGATCAGCA CCTGTCTGGA ATTCAGCATG
 61 GCCGACATCG TGATGACCCA GAGCCCCGAT AGCCTGGCCG TGTCTCTGGG AGAGAGAGCC
```

```
121 ACCATCAACT GCAAGGCCAG CCAGAGCGTG TCCAACGACG TGGCCTGGTA TCAGCAGAAG

181 CCCGGCCAGA GCCCTAAGCT GCTGATCTCC TACACCAGCA GCAGATATGC CGGCGTGCCC

241 GACAGATTTT CCGGCAGCGG CTCTGGCACC GACTTCACCC TGACAATCAG CTCCCTGCAG

301 GCCGAGGACG TGGCCGTGTA CTTCTGTCAG CAAGACTACA ACAGCCCCCC CACCTTCGGC

361 GGAGGCACCA AGCTGGAAAT CAAGCGGACA GTGGCCGCTC CAGCGTGTT CATCTTCCCA

421 CCTAGCGACG AGCAGCTGAA GTCCGGCACA GCCTCTGTCG TGTGCCTGCT GAACAACTTC

431 TACCCCCGCG AGGCCAAGGT GCAGTGGAAG GTGGACAATG CCCTGCAGAG CGGCAACAGC

541 CAGGAAAGCG TGACCGAGCA GGACAGCAAG GACTCCACCT ACAGCCTGAG CAGCACCCTG

601 ACCCTGAGCA AGGCCGACTA CGAGAAGCAC AAGGTGTACG CCTGCGAAGT GACCCACCAG

661 GGACTGAGCA GCCCTGTGAC CAAGAGCTTC AACCGGGGCG AGTGC
```

(germline leader sequence)  
SEQ ID NO: 13
```
  1 MDWTWRILFL VAAATGAHS
```

(natalizumab HC)  
SEQ ID NO: 14
```
  1 QVQLVQSGAE VKKPGASVKV SCKASGFNIK DTYIHWVRQA PGQRLEWMGR

51 IDPANGYTKY DPKFQGRVTI TADTSASTAY MELSSLRSED TAVYYCAREG

101 YYGNYGVYAM DYWGQGTLVT VSS
```

(natalizumab HC S225P, S375C)  
SEQ ID NO: 15
```
  1 ASTKGPSVFP LAPCSRSTSE STAALGCLVK DYFPEPVTVS WNSGALTSGV

51 HTFPAVLQSS GLYSLSSVVT VPSSSLGTKT YTCNVDHKPS NTKVDKRVES

101 KYGPPCPPCP APEFLGGPSV FLFPPKPKDT LMISRTPEVT CVVVDVSQED

151 PEVQFNWYVD GVEVHNAKTK PREEQFNSTY RVVSVLTVLH QDWLNGKEYK

201 CKVSNKGLPS SIEKTISKAK GQPREPQVYT LPPSQEEMTK NQVSLTCLVK

251 GFYPCDIAVE WESNGQPENN YKTTPPVLDS DGSFFLYSRL TVDKSRWQEG

301 NVFSCSVMHE ALHNHYTQKS LSLSLGK
```

(natalizumab HC S225P, S375C cDNA)  
SEQ ID NO: 16
```
  1 ATGGACTGGA CCTGGCGCAT CCTGTTTCTG GTGGCCGCTG CTACCGGCGC TCACTCCCAG

51 GTGCAGCTGG TGCAGTCTGG CGCCGAAGTG AAGAAACCTG GCGCCTCCGT GAAGGTGTCC

121 TGCAAGGCCT CCGGCTTCAA CATCAAGGAC ACCTACATCC ACTGGGTCCG ACAGGCCCCT

131 GGACAGCGGC TGGAATGGAT GGGCAGAATC GACCCCGCCA ACGGCTACAC TAAGTACGAC

241 CCCAAGTTCC AGGGCAGAGT GACCATCACC GCCGACACCT CCGCCTCCAC AGCCTACATG

301 GAACTGTCCT CCCTGCGGAG CGAGGACACC GCCGTGTACT ACTGCGCCAG AGAGGGCTAC

361 TACGGCAACT ACGGCGTGTA CGCCATGGAC TACTGGGGCC AGGGCACCCT GGTCACCGTG

421 TCCTCCGCTT CCACCAAGGG CCCCTCCGTG TTCCCTCTGG CCCCTTGCTC CCGGTCCACC

431 TCCGAGTCTA CCGCCGCTCT GGGCTGCCTG GTCAAGGACT ACTTCCCCGA GCCCGTGACC

541 GTGTCCTGGA ACTCTGGCGC CCTGACCTCT GGCGTGCACA CCTTCCCTGC TGTGCTGCAG

501 TCCTCCGGCC TGTACTCCCT GTCCTCCGTC GTGACCGTGC CCTCCAGCTC CCTGGGCACC

661 AAGACCTACA CCTGTAACGT GGACCACAAG CCCTCCAACA CCAAGGTGGA CAAGCGGGTG

721 GAATCTAAGT ACGGCCCTCC CTGCCCCCCC TGCCCTGCCC CTGAATTTCT GGGCGGACCT

781 TCCGTGTTCC TGTTCCCCCC AAAGCCCAAG GACACCCTGA TGATCTCCCG GACCCCCGAA

841 GTGACCTGCG TGGTGGTGGA CGTGTCCCAG GAAGATCCCG AGGTCCAGTT CAATTGGTAC

901 GTGGACGGCG TGGAAGTGCA CAACGCCAAG ACCAAGCCCA GAGAGGAACA GTTCAACTCC
```

-continued

```
 961 ACCTACCGGG TGGTGTCCGT GCTGACCGTG CTGCACCAGG ACTGGCTGAA CGGCAAAGAG

1021 TACAAGTGCA AGGTGTCCAA CAAGGGCCTG CCCAGCTCCA TCGAAAAGAC CATCTCCAAG

1081 GCCAAGGGAC AGCCTCGCGA GCCCCAGGTG TACACCCTGC CTCCAAGCCA GGAAGAGATG

1141 ACCAAGAACC AGGTGTCCCT GACCTGTCTG GTCAAGGGCT TCTACCCCTG CGATATCGCC

1201 GTGGAATGGG AGTCCAACGG CCAGCCCGAG AACAACTACA AGACCACCCC CCTGTGCTG

1251 GACTCCGACG GCTCCTTCTT CCTGTACTCT CGGCTGACCG TGGACAAGTC CCGGTGGCAG

1321 GAAGGCAACG TCTTCTCCTG CTCCGTGATG CACGAGGCCC TGCACAACCA CTACACCCAG

1381 AAGTCCCTGT CCCTGAGCCT GGGCAAG
```

(germline leader sequence)
<br>SEQ ID NO: 17
```
  1 MDMRVPAQLL GLLLLWLRGA RC
```

(natalizumab LC)
<br>SEQ ID NO: 18
```
  1 DIQMTQSPSS LSASVGDRVT ITCKTSQDIN KYMAWYQQTP GKAPRLLIHY

51 TSALQPGIPS RFSGSGSGRD YTFTISSLQP EDIATYYCLQ YDNLWTFGQG

101 TKVEIK
```

(natalizumab LC cDNA)
<br>SEQ ID NO: 19
```
  1 ATGGACATGA GAGTGCCCGC CCAGCTGCTG GGACTGCTGC TGCTGTGGCT GAGAGGCGCC

61 AGATGCGACA TCCAGATGAC CCAGTCCCCC TCCAGCCTGT CCGCCTCCGT GGGCGACAGA

121 GTGACCATCA CATGCAAGAC CTCCCAGGAC ATCAACAAGT ACATGGCCTG GTATCAGCAG

181 ACCCCCGGCA AGGCCCCTCG GCTGCTGATC CACTACACCT CCGCTCTGCA GCCTGGCATC

241 CCCTCCAGAT TCTCCGGCTC CGGCTCTGGC CGGGACTATA CCTTCACCAT CTCCAGTCTG

301 CAGCCCGAGG ATATCGCCAC CTACTACTGC CTGCAGTACG ACAACCTGTG GACCTTCGGC

361 CAGGGCACCA AGGTGGAAAT CAAGCGGACC GTGGCCGCTC CCTCCGTGTT CATCTTCCCA

421 CCCTCCGACG AGCAGCTGAA GTCCGGCACC GCCTCCGTCG TGTGCCTGCT GAACAACTTC

481 TACCCCCGCG AGGCCAAGGT GCAGTGGAAG GTGGACAACG CCCTGCAGTC CGGCAACTCC

541 CAGGAATCCG TCACCGAGCA GGACTCCAAG GACAGCACCT ACTCCCTGTC TCCACCCTG

601 ACCCTGTCCA AGGCCGACTA CGAGAAGCAC AAGGTGTACG CCTGCGAAGT GACCCACCAG

661 GGCCTGTCCA GCCCCGTGAC CAAGTCCTTC AACCGGGGCG AGTGC
```

---

The invention claimed is:

1. An antibody-drug conjugate compound (ADC), comprising an antibody or antigen binding fragment thereof, having an engineered cysteine at light chain position 41 (according to Kabat numbering); and
   a linker drug conjugated to said antibody or antigen binding fragment through said engineered cysteine.

2. The compound according to claim 1, wherein said linker drug comprises a cytotoxic drug selected from the group consisting of anthracyclines, duocarmycins, pyrrolobenzodiazepine (PBD) dimers, calicheamicins, maytansinoids, and auristatins.

3. The compound according to claim 2, wherein said cytotoxic drug is monomethyl auristatin E (MMAE) or emtansine (DM1).

4. The compound according to claim 2, wherein said cytotoxic drug is a duocarmycin derivative.

5. The compound according to claim 1, wherein the antibody or antigen binding fragment of said ADC further comprises an engineered cysteine at position 375 of the heavy chain (according to Eu numbering) and linker drug is conjugated through said engineered cysteine at position 375.

6. The compound according to claim 1, wherein said linker drug comprises a cleavable linker selected from valine-citrulline (vc) and valine-alanine (va).

7. The compound according to claim 2, wherein said linker drug comprises a cleavable linker selected from valine-citrulline (vc) and valine-alanine (va).

8. The compound according to claim 3, wherein said linker drug comprises a cleavable linker selected from valine-citrulline (vc) and valine-alanine (va).

9. The compound according to claim 4, wherein said linker drug comprises a cleavable linker selected from valine-citrulline (vc) and valine-alanine (va).

10. The compound according to claim 9, wherein said ADC has the formula (I)
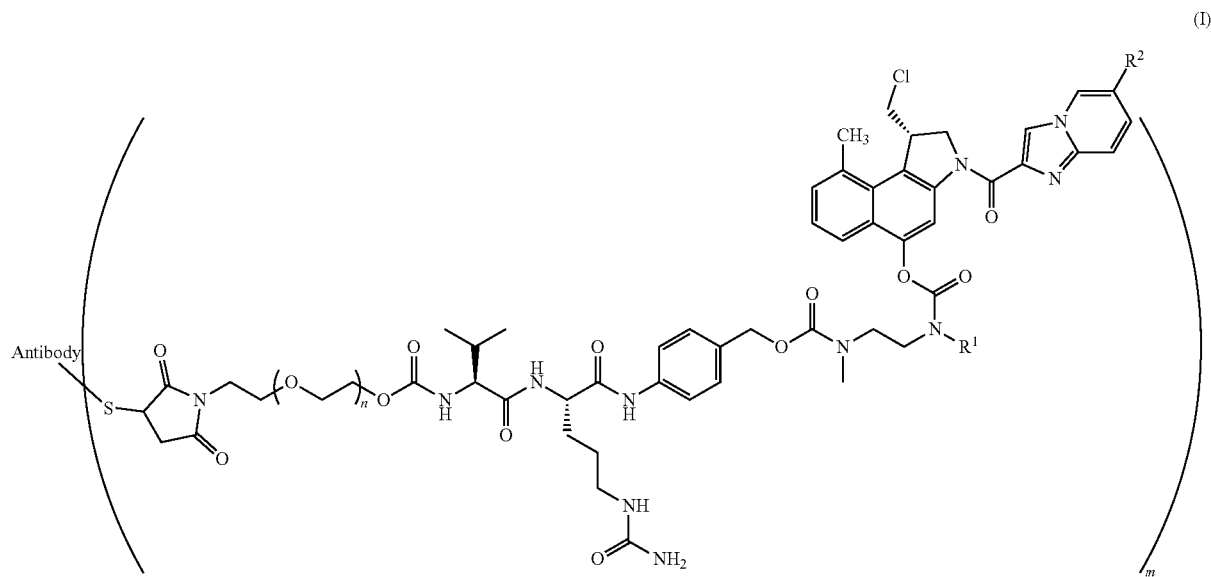
wherein said Antibody is the antibody or antigen binding fragment thereof that contains the engineered cysteine at light chain position 41,
n is 0, 1, 2, or 3,
m represents an average DAR of from 1 to 6,
$R^1$ is selected from the group consisting of
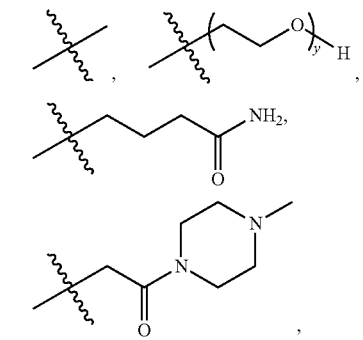
y is 1-16, and
$R^2$ is selected from the group consisting of
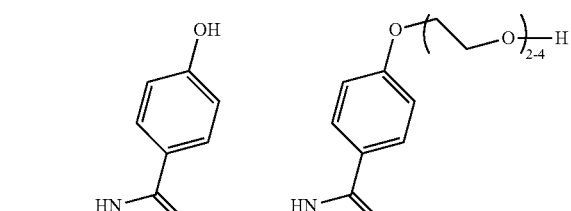

11. The compound according to claim 10, wherein
n is 0 or 1,
m represents an average DAR of from 1.5 to 2,
$R^1$ is

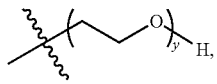

y is 1-4, and
$R^2$ is selected from the group consisting of

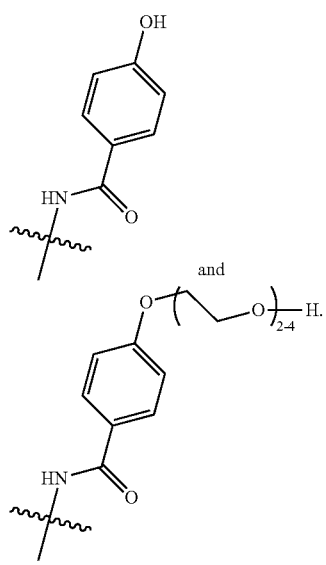

and

12. The compound according to claim 11, wherein said ADC has the formula (II)

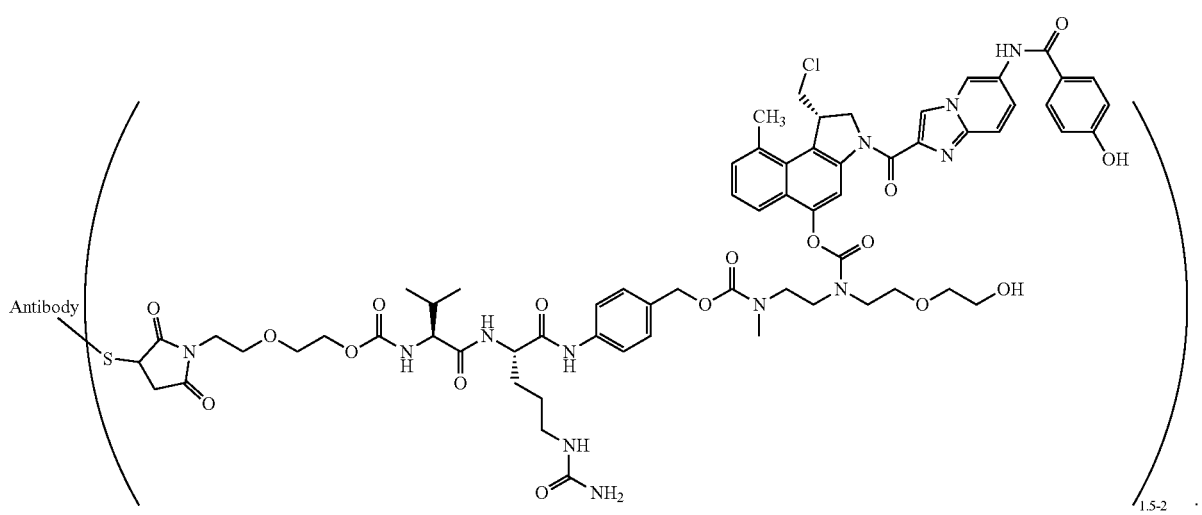

13. The compound according to claim 1, wherein said antibody or antigen binding fragment thereof is a monoclonal antibody or antigen binding fragment thereof.

14. The compound according to claim 13, wherein said antibody or antigen binding fragment thereof is a human or humanized IgG monoclonal antibody or antigen binding fragment thereof.

15. The compound according to claim 14, wherein said antibody or antigen binding fragment thereof has κ (kappa) light chains.

16. The compound according to claim 13, wherein said ADC comprises an antibody selected from the group consisting of an anti-annexin A1 antibody, an anti-CD115 antibody, an anti-CD123 antibody, an anti-CLL-1 antibody, an anti-c-MET antibody, an anti-MUC1 antibody, an anti-PSMA antibody, an anti-5T4 antibody and an anti-TF antibody.

17. The compound according to claim 16, wherein said antibody is an anti-PSMA monoclonal antibody, or an anti-5T4 monoclonal antibody.

18. The compound according to claim 17, wherein said antibody is an anti-5T4 monoclonal antibody that has a heavy chain that comprises the amino acid sequence of SEQ ID NO:8 and a light chain that comprises the amino acid sequence of SEQ ID NO:11.

19. The compound according to claim 17, wherein said antibody is an anti-PSMA monoclonal antibody that has a heavy chain that comprises the amino acid sequence of SEQ ID NO:2 and a light chain that comprises the amino acid sequence of SEQ ID NO:5.

\* \* \* \* \*

SEQUENCE LISTING

<160> NUMBER OF SEQ ID NOS: 19

<210> SEQ ID NO 1
<211> LENGTH: 21
<212> TYPE: PRT
<213> ORGANISM: Artificial Sequence
<220> FEATURE:
<223> OTHER INFORMATION: Leader sequence

<400> SEQUENCE: 1

```
Met Ala Cys Pro Gly Phe Leu Trp Ala Leu Val Ile Ser Thr Cys Leu
1               5                   10                  15

Glu Phe Ser Met Ala
            20
```

<210> SEQ ID NO 2
<211> LENGTH: 115

```
<212> TYPE: PRT
<213> ORGANISM: Artificial Sequence
<220> FEATURE:
<223> OTHER INFORMATION: Heavy chain variable region of anti-PSMA
      antibody

<400> SEQUENCE: 2

Glu Val Gln Leu Val Gln Ser Gly Ala Glu Val Lys Lys Pro Gly Ala
1               5                   10                  15

Ser Val Lys Ile Ser Cys Lys Thr Ser Gly Tyr Thr Phe Thr Glu Tyr
            20                  25                  30

Thr Ile His Trp Val Lys Gln Ala Cys Gly Lys Gly Leu Glu Trp Ile
        35                  40                  45

Gly Asn Ile Asn Pro Asn Asn Gly Gly Thr Thr Tyr Asn Gln Lys Phe
    50                  55                  60

Glu Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Val Thr
            100                 105                 110

Val Ser Ser
        115

<210> SEQ ID NO 3
<211> LENGTH: 330
<212> TYPE: PRT
<213> ORGANISM: Artificial Sequence
<220> FEATURE:
<223> OTHER INFORMATION: Heavy chain constant region of anti-PSMA
      antibody

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 4
<211> LENGTH: 1398
<212> TYPE: DNA
<213> ORGANISM: Artificial Sequence
<220> FEATURE:
<223> OTHER INFORMATION: cDNA sequence of heavy chain of anti-PSMA
      antibody

<400> SEQUENCE: 4
atggcctgtc ctggatttct gtgggccctc gtgatcagca cctgtctgga attcagcatg      60
gccgaggtgc agctggtgca gtctggcgcc gaagtgaaga accaggcgc cagcgtgaag     120 atcagctgca agaccagcgg ctacaccttc accgagtaca ccatccactg ggtcaagcag     180
gcctgtggca agggcctgga atggatcggc aacatcaacc caacaacgg cggcaccacc     240 tacaaccaga agttcgagga ccgggccacc ctgaccgtgg acaagagcac aagcaccgcc     300
tacatggaac tgagcagcct gcggagcgag gacaccgccg tgtactattg tgccgccgga     360
tggaacttcg actactgggg ccagggcacc accgtgacag tgtctagcgc cagcacaaag     420
ggccccagcg tgttccctct ggcccctagc agcaagtcta cctctggcgg aacagccgcc     480
ctgggctgcc tcgtgaagga ctactttccc gagcccgtga ccgtgtcctg aactctggc     540 gctctgacaa gcggcgtgca cacctttcca gccgtgctgc agagcagcgg cctgtactct     600
ctgagcagcg tcgtgactgt gcccagcagc agcctgggca cccagaccta catctgcaac     660
gtgaaccaca gcccagcaa caccaaggtg gacaaaaagg tggaacccaa gagctgcgac     720
aagacccaca cctgtccccc ttgtcctgcc ctgaactgc tgggcggacc ttccgtgttc     780
ctgttccccc caaagcccaa ggacaccctg atgatcagcc ggaccccga agtgacctgc     840 gtggtggtgg atgtgtccca cgaggaccct gaagtgaagt tcaattggta cgtggacggc     900
gtggaagtgc acaacgccaa gaccaagccc agagaggaac agtacaacag cacctaccgg     960
gtggtgtccg tgctgacagt gctgcaccag gactggctga acggcaaaga gtacaagtgc    1020
aaggtgtcca acaaggccct gcctgccccc atcgagaaaa ccatcagcaa ggccaagggc    1080
cagccccgcg aacccaggt gtacacactg cctcccagca gggacgagct gaccaagaac    1140
caggtgtccc tgacatgcct cgtgaaaggc ttctaccct ccgatatcgc cgtggaatgg    1200
gagagcaacg gccagcccga gaacaactac aagaccaccc ccctgtgct ggacagcgac    1260
```

-continued

```
ggctcattct tcctgtacag caagctgact gtggataagt cccggtggca gcagggcaac    1320
gtgttcagct gcagcgtgat gcacgaggcc ctgcacaacc actacaccca gaaaagcctg    1380
tccctgagcc ccggcaag                                                   1398
```

<210> SEQ ID NO 5
<211> LENGTH: 107
<212> TYPE: PRT
<213> ORGANISM: Artificial Sequence
<220> FEATURE:
<223> OTHER INFORMATION: Light chain variable region of anti-PSMA
     antibody

<400> SEQUENCE: 5

```
Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Asn Ser Tyr Pro Leu
                85                  90                  95

Thr Phe Gly Gly Gly Thr Lys Leu Glu Ile Lys
            100                 105
```

<210> SEQ ID NO 6
<211> LENGTH: 107
<212> TYPE: PRT
<213> ORGANISM: Artificial Sequence
<220> FEATURE:
<223> OTHER INFORMATION: Light chain constant region of anti-PSMA
     antibody

<400> SEQUENCE: 6

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 7
<211> LENGTH: 705
<212> TYPE: DNA
<213> ORGANISM: Artificial Sequence
<220> FEATURE:
<223> OTHER INFORMATION: cDNA sequence of light chain of anti-PSMA
     antibody

<400> SEQUENCE: 7

```
atggcttgtc ctggatttct gtgggccctc gtgatcagca cctgtctgga attcagcatg      60
gccgacatcg tgatgaccca gagccccagc tctctgagcg ccagcgtggg cgacagagtg     120
accatcacat gcaaggccag ccaggacgtg ggcaccgccg tggattggta tcagcagaag     180
cctggcaagg cccccaagct gctgatctac tgggccagca ccagacacac cggcgtgccc     240
gatagattca caggcagcgg ctccggcacc gacttcaccc tgacaatcag cagcctgcag     300
cccgaggact cgccgactac cttctgccag cagtacaaca gctaccccct gaccttcggc     360
ggaggcacca agctggaaat caagcggaca gtggccgctc ccagcgtgtt catcttccca     420
cctagcgacg agcagctgaa gtctggcacc gcctctgtcg tgtgcctgct gaacaacttc     480
taccccgcg aggccaaggt gcagtggaag gtggacaatg ccctgcagag cggcaacagc      540
caggaaagcg tgaccgagca ggacagcaag gactccacct acagcctgag cagcaccctg     600
accctgagca aggccgacta cgagaagcac aaggtgtacg cctgcgaagt gacccaccag     660
ggcctgtcta gccccgtgac caagagcttc aaccggggcg agtgc                     705
```

<210> SEQ ID NO 8
<211> LENGTH: 120
<212> TYPE: PRT
<213> ORGANISM: Artificial Sequence
<220> FEATURE:
<223> OTHER INFORMATION: H8 HC P41C

<400> SEQUENCE: 8

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Lys Gln Ser Cys Gly Gln Gly Leu Glu Trp Ile
        35                  40                  45

Gly Arg Ile Asn Pro Asn Asn Gly Val Thr Leu Tyr Asn Gln Lys Phe
    50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Leu Val Thr Val Ser Ser
        115                 120
```

<210> SEQ ID NO 9
<211> LENGTH: 330
<212> TYPE: PRT
<213> ORGANISM: Artificial Sequence
<220> FEATURE:
<223> OTHER INFORMATION: human IgG1 antibody HC constant region

<400> SEQUENCE: 9

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 10
<211> LENGTH: 1413
<212> TYPE: DNA
<213> ORGANISM: Artificial Sequence
<220> FEATURE:
<223> OTHER INFORMATION: H8 HC P41C cDNA

<400> SEQUENCE: 10
atggcctgtc ctggatttct gtgggccctc gtgatcagca cctgtctgga attcagcatg      60
gcccaggtgc agctggtgca gtctggcgcc gaagtgaaga accaggcgc cagcgtgaag      120 gtgtcctgca aggccagcgg ctacagcttc accggctact acatgcactg ggtcaagcag      180
agctgcggcc agggcctgga atggatcggc agaatcaacc ccaacaacgg cgtgaccctg      240
tacaaccaga aattcaagga ccgcgtgacc atgacccggg acaccagcat cagcaccgcc      300
tacatggaac tgagccggct gagaagcgac gacaccgccg tgtactactg cgcccggtcc      360
accatgatca ccaactacgt gatggactac tggggccagg gcaccctcgt gacagtgtct      420

| | |
|---|---|
| agcgccagca caaagggccc cagcgtgttc cctctggccc ctagcagcaa gagcacatct | 480 |
| ggcggaacag ccgccctggg ctgcctcgtg aaggattact ccccgagcc cgtgaccgtg | 540 |
| tcctggaata gcggagccct gacaagcggc gtgcacacct tccagccgt gctgcagagc | 600 |
| agcggcctgt actctctgag cagcgtcgtg actgtgccca gcagcagcct gggcacccag | 660 |
| acctacatct gcaacgtgaa ccacaagccc agcaacacca aggtggacaa gaaggtggaa | 720 |
| cccaagagct gcgacaagac ccacacctgt cccccttgtc ctgcccctga actgctgggc | 780 |
| ggaccttccg tgttcctgtt cccccaaag cccaaggaca ccctgatgat cagccggacc | 840 |
| cccgaagtga cctgcgtggt ggtggatgtg tcccacgagg accctgaagt gaagttcaat | 900 |
| tggtacgtgg acggcgtgga agtgcacaac gccaagacca gcccagaga ggaacagtac | 960 |
| aacagcacct accgggtggt gtccgtgctg acagtgctgc accaggactg gctgaacggc | 1020 |
| aaagagtaca agtgcaaggt gtccaacaaa gccctgcctg cccccatcga gaaaaccatc | 1080 |
| agcaaggcca agggccagcc ccgcgaaccc caggtgtaca cactgcctcc cagccgggaa | 1140 |
| gagatgacca agaaccaggt gtccctgaca tgcctcgtga aaggcttcta ccctcccgat | 1200 |
| atcgccgtgg aatgggagag caacggccag cccgagaaca actacaagac cacccccct | 1260 |
| gtgctggaca gcgacggctc attcttcctg tacagcaagc tgaccgtgga caagtcccgg | 1320 |
| tggcagcagg gcaacgtgtt cagctgcagc gtgatgcacg aggccctgca caaccactac | 1380 |
| acccagaagt ccctgagcct gagccccggc aaa | 1413 |

<210> SEQ ID NO 11
<211> LENGTH: 107
<212> TYPE: PRT
<213> ORGANISM: Artificial Sequence
<220> FEATURE:
<223> OTHER INFORMATION: H8 LC

<400> SEQUENCE: 11

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Ser Tyr Thr Ser Ser Arg Tyr Ala Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Phe Cys Gln Gln Asp Tyr Asn Ser Pro Pro
                85                  90                  95

Thr Phe Gly Gly Gly Thr Lys Leu Glu Ile Lys
            100                 105

<210> SEQ ID NO 12
<211> LENGTH: 705
<212> TYPE: DNA
<213> ORGANISM: Artificial Sequence
<220> FEATURE:
<223> OTHER INFORMATION: H8 LC cDNA

<400> SEQUENCE: 12

| | |
|---|---|
| atggcctgtc ctggatttct gtgggccctc gtgatcagca cctgtctgga attcagcatg | 60 |
| gccgacatcg tgatgaccca gagccccgat agcctggccg tgtctctggg agagagagcc | 120 |

-continued

```
accatcaact gcaaggccag ccagagcgtg tccaacgacg tggcctggta tcagcagaag    180
cccggccaga gccctaagct gctgatctcc tacaccagca gcagatatgc cggcgtgccc    240
gacagatttt ccggcagcgg ctctggcacc gacttcaccc tgacaatcag ctccctgcag    300
gccgaggacg tggccgtgta cttctgtcag caagactaca acagcccccc caccttcggc    360
ggaggcacca agctggaaat caagcggaca gtggccgctc ccagcgtgtt catcttccca    420
cctagcgacg agcagctgaa gtccggcaca gcctctgtcg tgtgcctgct gaacaacttc    480 taccccgcg aggccaaggt gcagtggaag gtggacaatg ccctgcagag cggcaacagc     540
caggaaagcg tgaccgagca ggacagcaag gactccacct acagcctgag cagcaccctg    600
accctgagca aggccgacta cgagaagcac aaggtgtacg cctgcgaagt gacccaccag    660
ggactgagca gccctgtgac caagagcttc aaccggggcg agtgc                    705
```

<210> SEQ ID NO 13
<211> LENGTH: 19
<212> TYPE: PRT
<213> ORGANISM: Artificial Sequence
<220> FEATURE:
<223> OTHER INFORMATION: germline leader sequence

<400> SEQUENCE: 13

Met Asp Trp Thr Trp Arg Ile Leu Phe Leu Val Ala Ala Ala Thr Gly
1               5                   10                  15

Ala His Ser

<210> SEQ ID NO 14
<211> LENGTH: 123
<212> TYPE: PRT
<213> ORGANISM: Artificial Sequence
<220> FEATURE:
<223> OTHER INFORMATION: natalizumab HC

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Arg Leu Glu Trp Met
        35                  40                  45

Gly Arg Ile Asp Pro Ala Asn Gly Tyr Thr Lys Tyr Asp Pro Lys Phe
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Tyr Gly Asn Tyr Gly Val Tyr Ala Met Asp Tyr
            100                 105                 110

Trp Gly Gln Gly Thr Leu Val Thr Val Ser Ser
        115                 120

<210> SEQ ID NO 15
<211> LENGTH: 327
<212> TYPE: PRT
<213> ORGANISM: Artificial Sequence
<220> FEATURE:
<223> OTHER INFORMATION: natalizumab HC S225P, S375C

<400> SEQUENCE: 15

-continued

```
Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Cys Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 16
<211> LENGTH: 1407
<212> TYPE: DNA
<213> ORGANISM: Artificial Sequence
<220> FEATURE:
<223> OTHER INFORMATION: natalizumab HC S225P, S375C cDNA

<400> SEQUENCE: 16

```
atggactgga cctggcgcat cctgtttctg gtggccgctg ctaccggcgc tcactcccag      60
gtgcagctgg tgcagtctgg cgccgaagtg aagaaacctg gcgcctccgt gaaggtgtcc     120
tgcaaggcct ccggcttcaa catcaaggac acctacatcc actgggtccg acaggcccct     180
```

```
ggacagcggc tggaatggat gggcagaatc gaccccgcca acggctacac taagtacgac    240
cccaagttcc agggcagagt gaccatcacc gccgacacct ccgcctccac agcctacatg    300
gaactgtcct ccctgcggag cgaggacacc gccgtgtact actgcgccag agagggctac    360
tacggcaact acgcgtgta cgccatggac tactggggcc agggcaccct ggtcaccgtg    420
tcctccgctt ccaccaaggg ccctccgtg ttccctctgg ccccttgctc ccggtccacc    480
tccgagtcta ccgccgctct gggctgcctg gtcaaggact acttccccga gcccgtgacc    540
gtgtcctgga actctggcgc cctgacctct ggcgtgcaca ccttccctgc tgtgctgcag    600
tcctccggcc tgtactccct gtcctccgtc gtgaccgtgc cctccagctc cctgggcacc    660
aagacctaca cctgtaacgt ggaccacaag ccctccaaca ccaaggtgga caagcgggtg    720
gaatctaagt acggcccctcc ctgccccccc tgccctgccc ctgaatttct gggcggacct    780
tccgtgttcc tgttcccccc aaagcccaag gacaccctga tgatctcccg gaccccgaa    840 gtgacctgcg tggtggtgga cgtgtcccag gaagatcccg aggtccagtt caattggtac    900
gtggacggcg tggaagtgca caacgccaag accaagccca gagaggaaca gttcaactcc    960
acctaccggg tggtgtccgt gctgaccgtg ctgcaccagg actggctgaa cggcaaagag   1020
tacaagtgca aggtgtccaa caagggcctg cccagctcca tcgaaaagac catctccaag   1080
gccaagggac agcctcgcga gccccaggtg tacaccctgc ctccaagcca ggaagagatg   1140
accaagaacc aggtgtccct gacctgtctg gtcaagggct ctaccccctg cgatatcgcc   1200
gtggaatggg agtccaacgg ccagcccgag aacaactaca agaccacccc cctgtgctg   1260 gactccgacg gctccttctt cctgtactct cggctgaccg tggacaagtc ccggtggcag   1320
gaaggcaacg tcttctcctg ctccgtgatg cacgaggccc tgcacaacca ctacacccag   1380
aagtccctgt ccctgagcct gggcaag                                        1407
```

<210> SEQ ID NO 17
<211> LENGTH: 22
<212> TYPE: PRT
<213> ORGANISM: Artificial Sequence
<220> FEATURE:
<223> OTHER INFORMATION: germline leader sequence

<400> SEQUENCE: 17

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 18
<211> LENGTH: 106
<212> TYPE: PRT
<213> ORGANISM: Artificial Sequence
<220> FEATURE:
<223> OTHER INFORMATION: natalizumab LC

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Thr Ser Gln Asp Ile Asn Lys Tyr
            20                  25                  30

Met Ala Trp Tyr Gln Gln Thr Pro Gly Lys Ala Pro Arg Leu Leu Ile
        35                  40                  45

His Tyr Thr Ser Ala Leu Gln Pro Gly Ile Pro Ser Arg Phe Ser Gly
    50                  55                  60

Ser Gly Ser Gly Arg Asp Tyr Thr Phe Thr Ile Ser Ser Leu Gln Pro
 65                  70                  75                  80

Glu Asp Ile Ala Thr Tyr Tyr Cys Leu Gln Tyr Asp Asn Leu Trp Thr
                 85                  90                  95

Phe Gly Gln Gly Thr Lys Val Glu Ile Lys
            100                 105

<210> SEQ ID NO 19
<211> LENGTH: 704
<212> TYPE: DNA
<213> ORGANISM: Artificial Sequence
<220> FEATURE:
<223> OTHER INFORMATION: natalizumab LC cDNA

<400> SEQUENCE: 19

```
atggacatga gagtgcccgc ccagctgctg ggactgctgc tgctgtggct gagaggcgcc        60
agatgcgaca tccagatgac ccagtccccc tccagcctgt ccgcctccgt gggcgacaga       120
gtgaccatca catgcaagac ctcccaggac atcaacaagt acatggcctg gtatcagcag       180
acccccggca aggcccctcg gctgctgatc cactacacct ccgctctgca gcctggcatc       240
ccctccagat tctccggctc cggctctggc cgggactata ccttcaccat ctccagtctg       300
cagcccgagg atatcgccac ctactactgc ctgcagtacg acaacctgtg gaccttcggc       360
cagggcacca aggtggaaat caagcggacc gtggccgctc cctccgtgtt catcttccca       420
ccctccgacg agcagctgaa gtccggcacc gcctccgtcg tgtgcctgct gaacaacttc       480 taccccgcg aggccaaggt gcagtggaag gtggacaacg ccctgcagtc cggcaactcc        540
caggaatccg tcaccgagca ggactccaag gacagcacct actccctgtc tccaccctga       600
ccctgtccaa ggccgactac gagaagcaca aggtgtacgc ctgcgaagtg acccaccagg       660
gcctgtccag ccccgtgacc aagtccttca ccggggcga gtgc                        704
```